United States Patent [19]
Venkatesan et al.

[11] Patent Number: 5,521,173
[45] Date of Patent: May 28, 1996

[54] TRICYCLIC BENZAZEPINE VASOPRESSIN ANTAGONISTS

[75] Inventors: Aranapakam M. Venkatesan, Elmhurst; Jay D. Albright, Nanuet; George T. Grosu, Pearl River, all of N.Y.

[73] Assignee: American Home Products Corporation, Madison, N.J.

[21] Appl. No.: 373,125

[22] Filed: Jan. 17, 1995

[51] Int. Cl.$^6$ .................... C07D 487/04; A61K 31/55
[52] U.S. Cl. .................... 514/220; 540/558; 540/561; 540/562; 544/344
[58] Field of Search .................... 540/558, 561, 540/562; 514/220

[56] References Cited

U.S. PATENT DOCUMENTS

| | | | |
|---|---|---|---|
| 3,763,183 | 10/1973 | Carabateas | 260/326.3 |
| 4,766,108 | 8/1988 | Ali | 514/16 |
| 5,055,448 | 10/1991 | Manning et al. | 514/16 |
| 5,070,187 | 12/1991 | Gavras et al. | 530/315 |
| 5,258,510 | 11/1993 | Ogawa et al. | 540/476 |

FOREIGN PATENT DOCUMENTS

| | | |
|---|---|---|
| 0382185 | 2/1990 | European Pat. Off. . |
| 0470514 | 8/1991 | European Pat. Off. . |
| 0514667 | 4/1992 | European Pat. Off. . |
| 0533242 | 9/1992 | European Pat. Off. . |
| 0533240 | 9/1992 | European Pat. Off. . |
| 0533243 | 9/1992 | European Pat. Off. . |
| 0533244 | 9/1992 | European Pat. Off. . |
| 0620216 | 4/1994 | European Pat. Off. . |
| 9105549 | 5/1991 | WIPO . |
| 9404525 | 3/1994 | WIPO . |
| 9414796 | 7/1994 | WIPO . |
| 9420473 | 9/1994 | WIPO . |
| 9412476 | 9/1994 | WIPO . |

OTHER PUBLICATIONS

J. Med. Chem., 1992, 35, 3905–3918, Williams et al.
J. Med. Chem., 1992, 35, 3895–3904—Manning et al.
J. Med. Chem., 1992, 35, 382–388, Manning et al.
From Vasopressin Antagonist to Agonist, DN+P4 (4), May 1991, Ruffolo et al., pp. 217–221.
Br. J. Pharmacol. (1992), 105, 787–791, Yamamura et al.
Science, vol. 252, pp. 572–574, Yamamura et al. (1991).
J. Med. Chem., 1992, 35, 3919–3927, Evans et al.
J. Med. Chem., 1993, 36, 3993–4005, Evans et al.

*Primary Examiner*—Philip I. Datlow
*Attorney, Agent, or Firm*—Steven R. Eck

[57] ABSTRACT

Tricyclic diazepines of the Formula I:

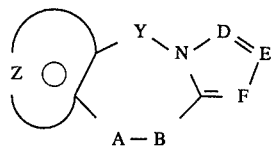

Formula I wherein A, B, D, E, F, Y, and Z are defined in the specification which compounds have vasopressin and oxytocin antagonist activity.

28 Claims, No Drawings

5,521,173

TRICYCLIC BENZAZEPINE VASOPRESSIN ANTAGONISTS

1. FIELD OF THE INVENTION

This invention relates to new tricyclic non-peptide vasopressin antagonists which are useful in treating conditions where decreased vasopressin levels are desired, such as in congestive heart failure, in disease conditions with excess renal water reabsorption and in conditions with increased vascular resistance and coronary vasoconstriction.

2. BACKGROUND OF THE INVENTION

Vasopressin is released from the posterior pituitary either in response to increased plasma osmolarity detected by brain osmoreceptors or decreased blood volume and blood pressure sensed by low-pressure volume receptors and arterial baroreceptors. The hormone exerts its action through two well defined receptor subtypes: vascular $V_1$ and renal epithelial $V_2$ receptors. Vasopressin-induced antidiuresis, mediated by renal epithelial $V_2$ receptors, helps to maintain normal plasma osmolarity, blood volume and blood pressure.

Vasopressin is involved in some cases of congestive heart failure where peripheral resistance is increased. $V_1$ antagonists may decrease systemic vascular resistance, increase cardiac output and prevent vasopressin induced coronary vasoconstriction. Thus, in conditions with vasopressin induce increases in total peripheral resistance and altered local blood flow, $V_1$-antagonists may be therapeutic agents. $V_1$ antagonists may decrease blood pressure, induced hypotensive effects and thus be therapeutically useful in treatment of some types of hypertension.

The blockage of $V_2$ receptors is useful in treating diseases characterized by excess renal reabsorption of free water. Antidiuresis is regulated by the hypothalamic release of vasopressin (antidiuretic hormone) which binds to specific receptors on renal collecting tubule cells. This binding stimulates adenylyl cyclase and promotes the cAMP-mediated incorporation of water pores into the luminal surface of these cells. $V_2$ antagonists may correct the fluid retention in congestive heart failure, liver cirrhosis, nephritic syndrome, central nervous system injuries, lung disease and hyponatremia.

Elevated vasopressin levels occur in congestive heart failure which is more common in older patients with chronic heart failure. In patients with hyponatremic congestive heart failure and elevated vasopressin levels, a $V_2$ antagonist may be beneficial in promoting free water excretion by antagonizing the action of antidiuretic hormone, On the basis of biochemical and pharmacological effects of the hormone, antagonists of vasopressin are expected to be therapeutically useful in the treatment and/or prevention of hypertension, cardiac insufficiency, coronary vasospasm, cardiac ischemia, renal vasospasm, liver cirrhosis, congestive heart failure, nephritic syndrome, brain edema, cerebral ischemia, cerebral hemorrhage-stroke, thrombosis-bleeding and abnormal states of water retention.

The following prior art references describe peptide vasopressin antagonists: M. Manning et al., *J. Med. Chem.*, 35, 382(1992); M. Manning et al., *J. Med. Chem.*, 35, 3895(1992); H. Gavras and B. Lammek, U.S. Pat. No. 5,070,187 (1991); M. Manning and W. H. Sawyer, U.S. Pat. No. 5,055,448(1991) F. E. Ali, U.S. Pat. No. 4,766,108(1988); R. R. Ruffolo et al., *Drug News and Perspective*, 4(4), 217, (May)(1991). P. D. Williams et al., have reported on potent hexapeptide oxytocin antagonists [*J. Med. Chem.*, 35, 3905(1992)] which also exhibit weak vasopressin antagonist activity in binding to $V_1$ and $V_2$ receptors. Peptide vasopressin antagonists suffer from a lack of oral activity and many of these peptides are not selective antagonists since they also exhibit partial agonist activity.

Non-peptide vasopressin antagonists have recently been disclosed, Y. Yamamura et al., *Science*, 252, 579(1991); Y. Yamamura et al., *Br. J. Pharmacol*, 105, 787(1992); Ogawa et al., (Otsuka Pharm Co., LTD.) EP 0514667-A1; EPO 382185-A2; WO9105549 and U.S. Pat. No. 5,258,510; WO 9404525 Yamanouchi Pharm. Co., Ltd., WO 9420473; WO 9412476; WO 9414796; Fujisawa Co. Ltd., EP 620216-A1 Ogawa et al, (Otsuka Pharm. Co.) EP 470514A disclose carbostyril derivatives and pharmaceutical compositions containing the same. Non-peptide oxytocin and vasopressin antagonist have been disclosed by Merck and Co.; M. G. Bock and P. D. Williams, EP 0533242A; M. G. Bock et al., EP 0533244A; J. M. Erb, D. F. Verber, P. D. Williams, EP 0533240A; K. Gilbert et al., EP 0533243A.

Premature birth can cause infant health problems and mortality and a key mediator in the mechanism of labor is the peptide hormone oxytocin. On the basis of the pharmacological action of oxytocin, antagonists of this hormone are useful in the prevention of preterm labor, B. E. Evans et al., *J. Med. Chem.* 35, 3919(1992), *J. Med. Chem.*, 36, 3993(1993) and references therein. The compounds of this invention are antagonists of the peptide hormone oxytocin and are useful in the control of premature birth.

The present invention relates to novel tricyclic derivatives which exhibit antagonist activity at $V_1$ and/or $V_2$ receptors and exhibit in vivo vasopressin antagonist activity. The compounds also exhibit antagonist activity at oxytocin receptors.

SUMMARY OF THE INVENTION

This invention relates to new compounds selected from those of the general formula I:

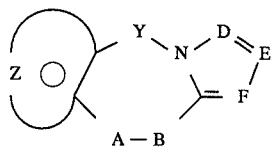

FORMULA I wherein Y is a moiety selected from; —$(CH_2)_n$— wherein n is an integer 0 or 1, and A—B is a moiety selected from

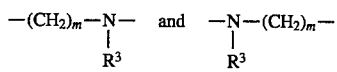

wherein m is an integer from 1 to 2; and the moiety:

represents: (1) phenyl or substituted phenyl optionally substituted by one or two substitutents selected from $(C_1-C_3)$lower alkyl, halogen, amino, $(C_1-C_3)$lower alkoxy or $(C_1-C_3)$lower alkylamino; (2) a 5-membered aromatic (unsaturated) heterocyclic ring having one heteroatom selected from O, N or S; (3) a 6-membered aromatic (unsaturated) heterocyclic ring having one nitrogen; (4) a 5 or 6-membered aromatic (unsaturated) heterocyclic ring having two nitrogen atoms; (5) a 5-membered aromatic (unsaturated) heterocyclic ring having one nitrogen atom together with either one oxygen or one sulfur atom; wherein the 5 or 6-membered heterocyclic rings are optionally substituted by $(C_1-C_3)$lower alkyl, halogen or $(C_1-C_3)$lower alkoxy;

the moiety:

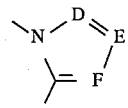

is a five membered aromatic(unsaturated) nitrogen containing heterocyclic ring wherein D, E and F are selected from carbon or nitrogen and wherein the carbon atoms may be optionally substituted by a substituent selected from halogen, $(C_1-C_3)$lower alkyl, hydroxy, $-COCl_3$, $-COCF_3$,

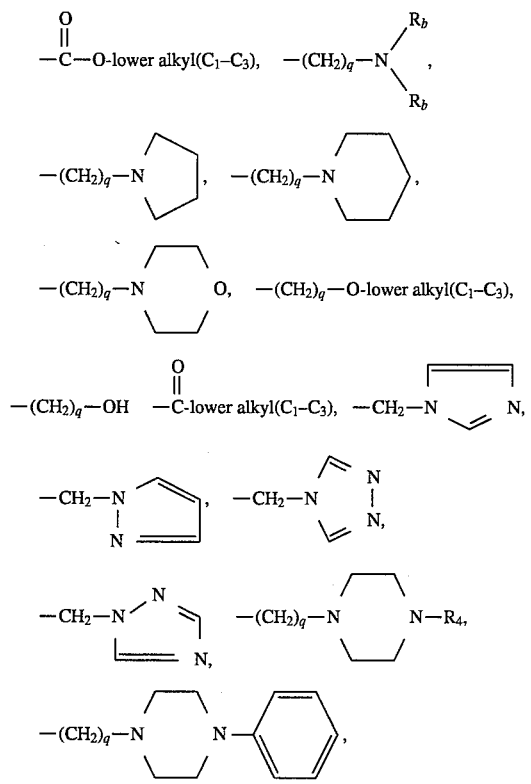

—CHO, amino, $(C_1-C_3)$lower alkoxy and $(C_1-C_3)$lower alkylamino, —CONH—$(C_1-C_3)$lower alkyl $(C_1-C_3)$, —CON[lower alkyl$(C_1-C_3)$]$_2$; q is one or two; $R_b$ is independently selected from hydrogen, —$CH_3$ and —$C_2H_5$; $R^3$ is a moiety of the formula:

wherein Ar is

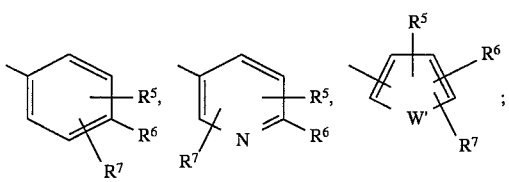

wherein $R^6$ is selected from

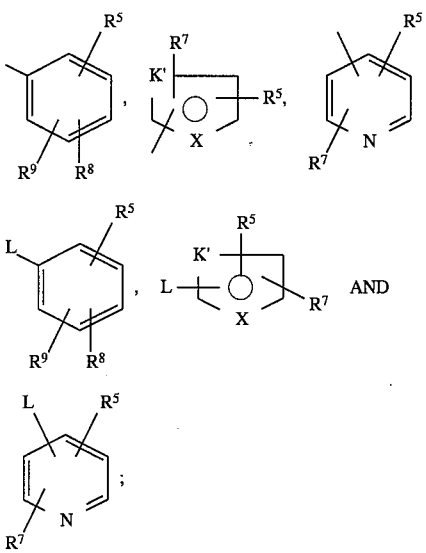

wherein L is O, S, SO, SO$_2$, —CO—, —CH$_2$—, —C≡C—;

K' is CH or N; X is O, S, N-lower alkyl$(C_1-C_3)$ and W' is selected from O, S, NH, N-lower alkyl$(C_1-C_3)$ and N-benzyl;

$R^4$ is selected from hydrogen, lower alkyl$(C_1-C_3)$, —CO— lower alkyl$(C_1-C_3)$; $R^1$ and $R^2$ are selected from hydrogen, $(C_1-C_3)$lower alkyl, $(C_1-C_3)$lower alkoxy and halogen;

$R^5$ is selected from hydrogen, lower alkyl$(C_1-C_3)$, lower alkoxy$(C_1-C_3)$ —O—CH$_2$—CH=CH$_2$ and halogen; $R^7$ is selected from hydrogen, lower alkyl$(C_1-C_3)$, halogen, O-lower alkyl$(C_1-C_3)$ and CF$_3$; $R^8$ and $R^9$ are independently selected from hydrogen, lower alkyl$(C_1-C_3)$, —S-lower alkyl$(C_1-C_3)$, halogen, —NH-lower alkyl$(C_1-C_3)$, —N-[lower alkyl$(C_1-C_3)$]$_2$, —OCF$_3$, —OH, —CN, —S—CF$_3$, —NO$_2$, —NH$_2$, O-lower alkyl $(C_1-C_3)$, CO-lower alkyl $(C_1-C_3)$ and CF$_3$; and the pharmaceutically acceptable salts thereof.

DETAILED DESCRIPTION OF THE INVENTION

Within the group of compounds defined by Formula I, certain subgroups of compounds are broadly preferred. Broadly preferred are those compounds wherein $R^3$ is the moiety:

and Ar is selected from the moiety

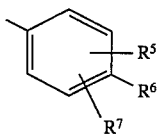

wherein $R^5$, $R^6$ and $R^7$ are as hereinbefore defined.

Especially preferred are compounds wherein $R^3$ is the moiety

and Ar is selected from the moiety

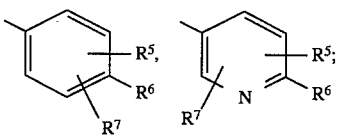

$R^6$ is

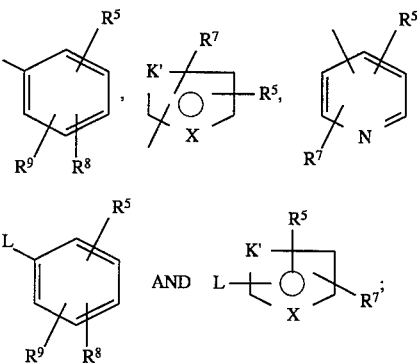

wherein K', X, L, $R^5$, $R^7$, $R^8$ and $R^9$ are as hereinbefore defined.

Also especially preferred are compounds where Y in Formula I is —(CH$_2$)$_n$— and n is zero or one; A—B is

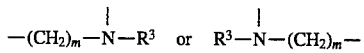

and K', X, L, $R^3$, $R^5$, $R^6$, $R^7$, $R^8$, and $R^9$ are as hereinbefore defined and m is an integer from 1–2.

The most preferred of the compounds of Formula I are those wherein Y is —(CH$_2$)$_n$— and n is one; A—B is

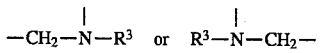

$R^3$ is a moiety

and Ar is selected from the moiety

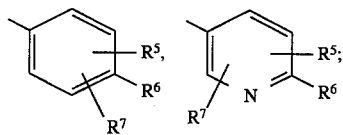

$R^6$ is

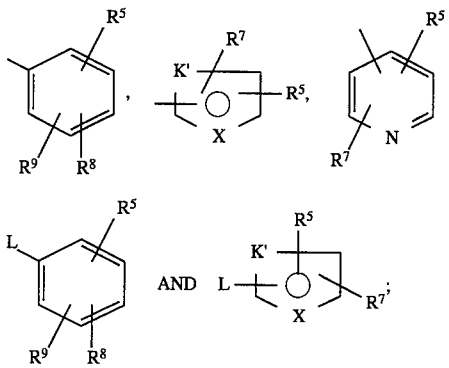

wherein K', X, L, $R^5$, $R^7$, $R^8$ and $R^9$ are as hereinbefore defined.

The most highly broadly preferred of the compounds of Formula I are those wherein Y is —(CH$_2$)$_n$— and n is one or zero; wherein the moiety

is a phenyl, substituted phenyl, thiophene, furan, pyrrole or pyridine ring;

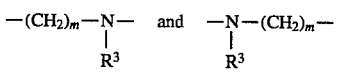

m is one when n is one and m is two when n is zero; D, E, F, K', L, X, $R^3$, $R^5$, $R^6$, $R^7$, $R^8$ and $R^9$ are as previously defined;

Especially preferred are compounds wherein $R^3$ is the moiety

and Ar is selected from the moiety

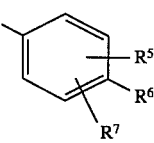

$R^6$ is

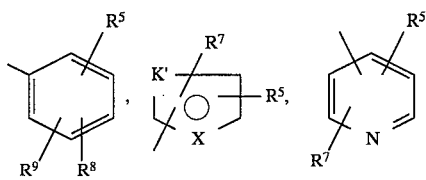

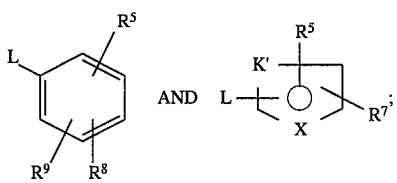

wherein K', L, X, $R^5$, $R^7$, $R^8$ and $R^9$ are as hereinbefore defined.

The especially preferred of the compounds of Formula I are those wherein Y is —$(CH_2)_n$— and n is one; A—B is

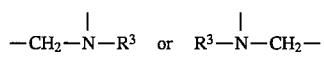

$R^3$ is a moiety

and Ar is selected from the moiety

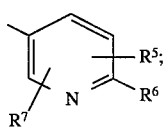

$R^6$ is

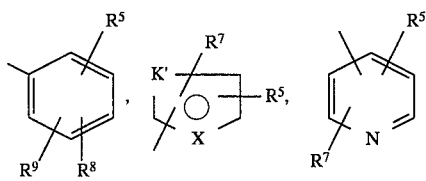

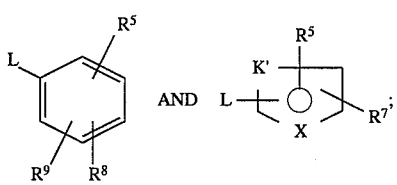

wherein K', X, L, $R^5$, $R^7$, $R^8$ and $R^9$ are as hereinbefore defined.

More particularly preferred are compounds of the formulae:

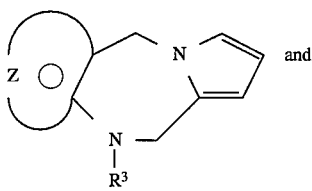

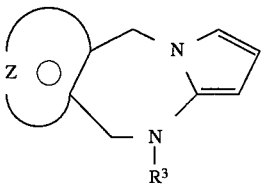

wherein the moiety:

is selected from a phenyl, thiophene, furan, pyrrole or pyridine ring;

wherein $R^3$ is the moiety

and Ar is selected from the moiety

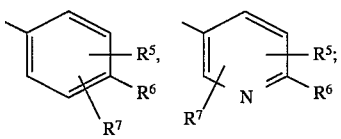

$R^6$ is

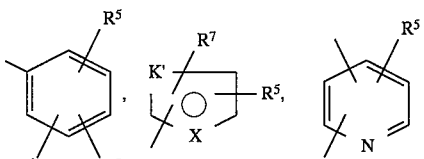

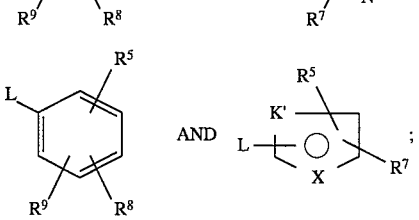

wherein K', L, X, $R^5$, $R^7$, $R^8$ and $R^9$ are as hereinbefore defined.

Also particularly preferred are compounds of the formulae:

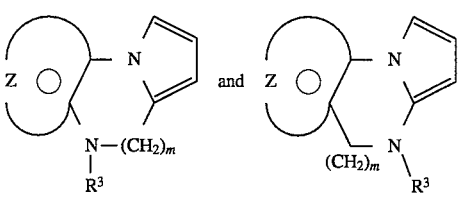

wherein m is two;

and the moiety

is selected from a phenyl, thiophene, furan, pyrrole or pyridine ring;
wherein $R^3$ is the moiety

and Ar is selected from the moiety

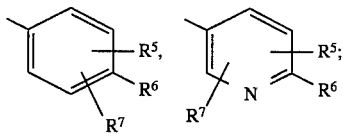

$R^6$ is

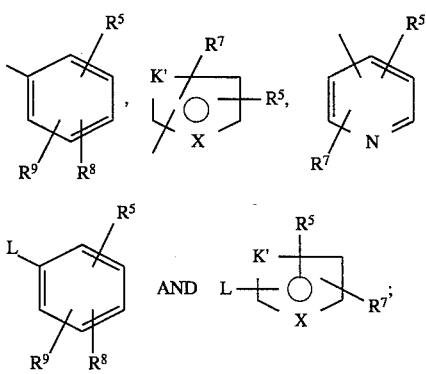

wherein K', L, X, $R^5$, $R^7$, $R^8$ and $R^9$ are as hereinbefore defined.

More particularly preferred are compounds of the formulae:

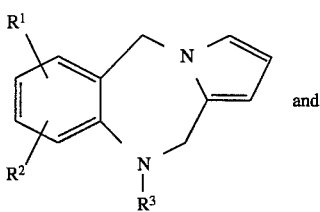

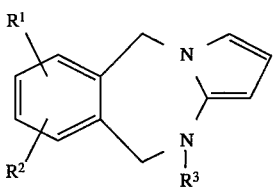

wherein $R^3$ is the moiety

and Ar is selected from the moiety

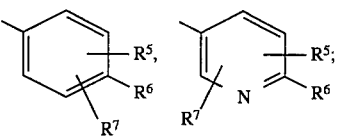

$R^6$ is

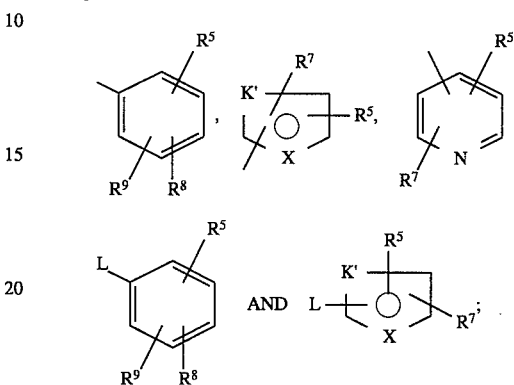

wherein K', L, X, $R^5$, $R^7$, $R^8$ and $R^9$ are as hereinbefore defined.

Also particularly preferred are compounds of the formulae:

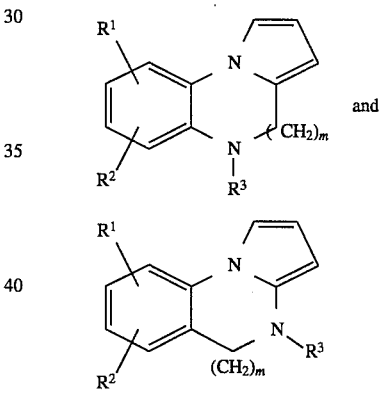

wherein $R^3$ is the moiety

and Ar is selected from the moiety

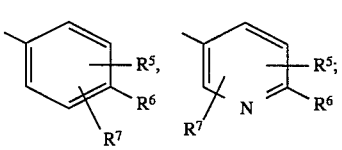

$R^6$ is

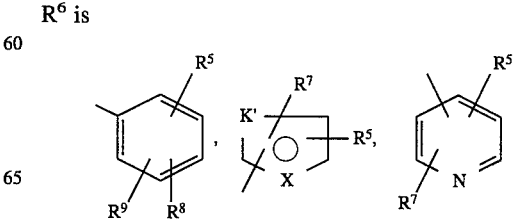

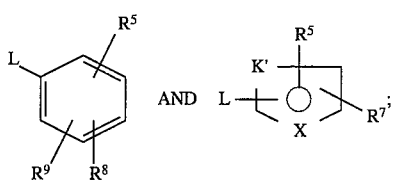

m is two;

wherein K', L, X, $R^5$, $R^7$, $R^8$ and $R^9$ are as hereinbefore defined.

More particularly preferred are compounds of the formulae:

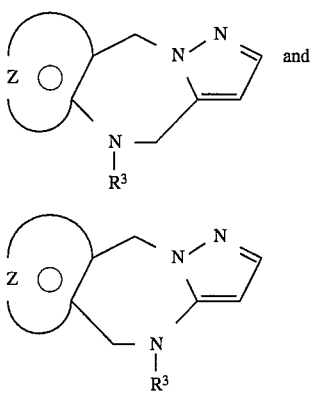

wherein the moiety:

is selected from a phenyl, thiophene, furan, pyrrole or pyridine ring;

wherein $R^3$ is the moiety

and Ar is selected from the moiety

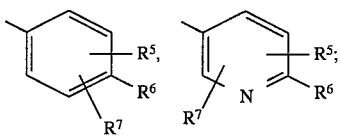

$R^6$ is

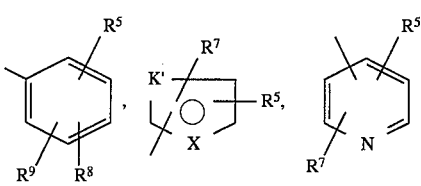

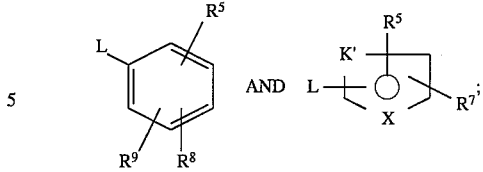

wherein K', L, X, $R^5$, $R^7$, $R^8$ and $R^9$ are as hereinbefore defined.

More particularly preferred are compounds of the formulae:

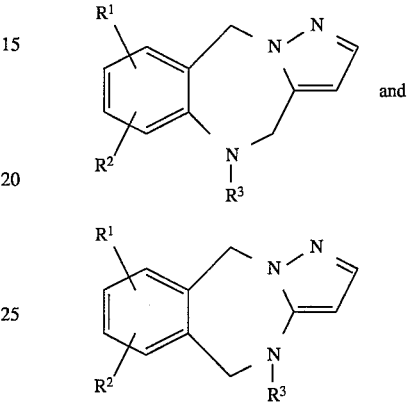

wherein $R^3$ is the moiety

and Ar is selected from the moiety

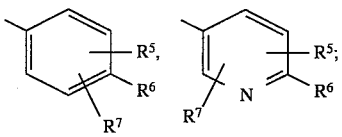

$R^6$ is

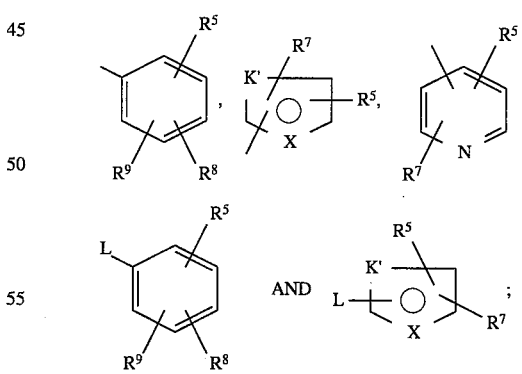

wherein K', L, X, $R^5$, $R^7$, $R^8$ and $R^9$ are as hereinbefore defined.

Compounds of this invention may be prepared as shown in Scheme I by reaction of tricyclic derivatives of Formula 3a and 3b wherein Z, Y, D, E, F and m are hereinbefore defined, with a substituted or unsubstituted 4-iodobenzoyl chloride 4a or a substituted or unsubstituted-6-iodopyridine-3-carbonyl chloride 4b wherein $R^5$ and $R^7$ are hereinbefore defined to give intermediates 5a and 5b. Reaction of 5a and 5b with tributyltin derivatives 8a, 8b or 8c where $R^5$, $R^7$, $R^8$, $R^9$, K', and X are hereinbefore defined affords 7a and 7b.

Compounds of structural type 8a, 8b, and 8c are prepared as shown in Scheme II from the corresponding bromo starting materials 6a, 6b, and 6c wherein $R^5$, $R^7$, $R^8$, $R^9$ and

SCHEME I

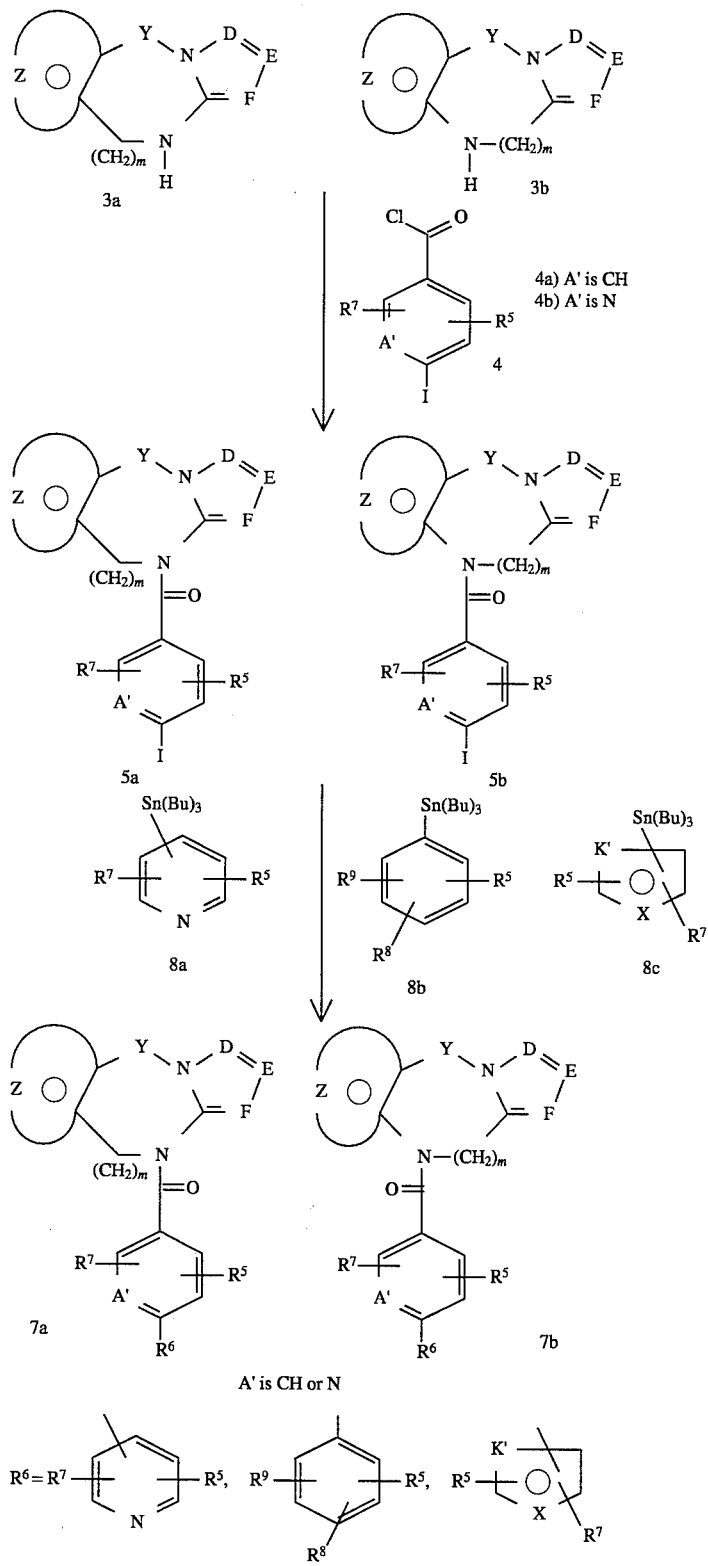

K' and X are hereinbefore defined, by first reacting with butyl lithium followed by reaction with tri-n-butyltin chloride to give the desired tin compound 8a, 8b and 8c.

SCHEME II

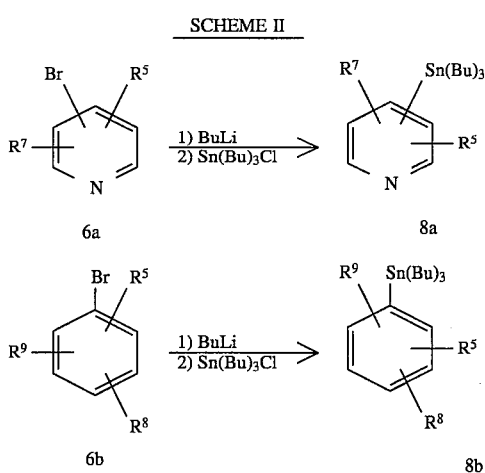

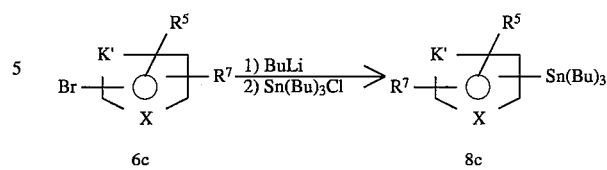

Alternatively, as shown in Scheme III, the bromo derivates 9a and 9b wherein A', Z, Y, D, E, F, $R^5$, $R^7$ and m are hereinbefore defined (prepared by reaction of 3a and 3b with acid chloride 8d wherein $R^5$, $R^7$ and A' are hereinbefore defined) are reacted with tetrakis(tri-phenylphosphine)palladium (O) and bis(tributyltin) in the presence of lithium chloride to give tin intermediate 11a and 11b. Further reaction of the tributyl tin derivatives 11a and 11b with bromo derivatives 10a, 10b or 10c, wherein M' is bromo or iodo and K', X, $R^5$, $R^7$, $R^8$ and $R^9$ are hereinbefore defined, in the presence of tetrakistriphenylphosphine palladium (O) gives 12a and 12b.

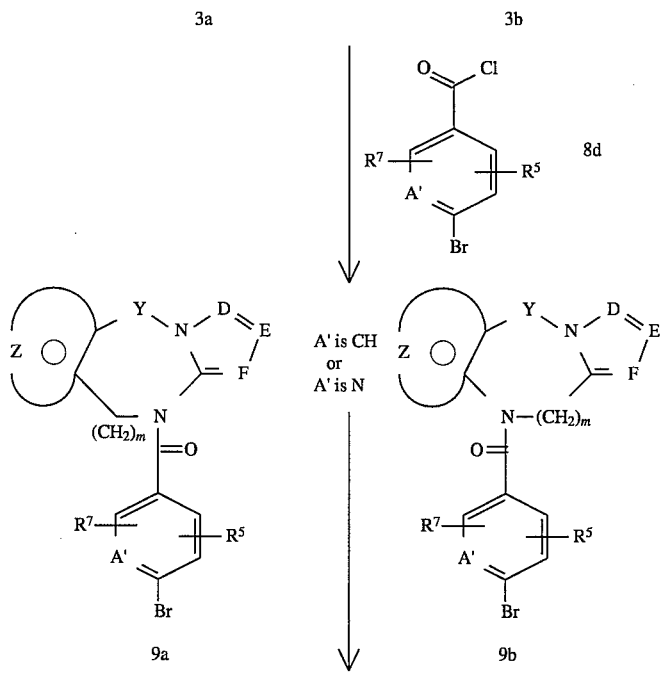

-continued
SCHEME III

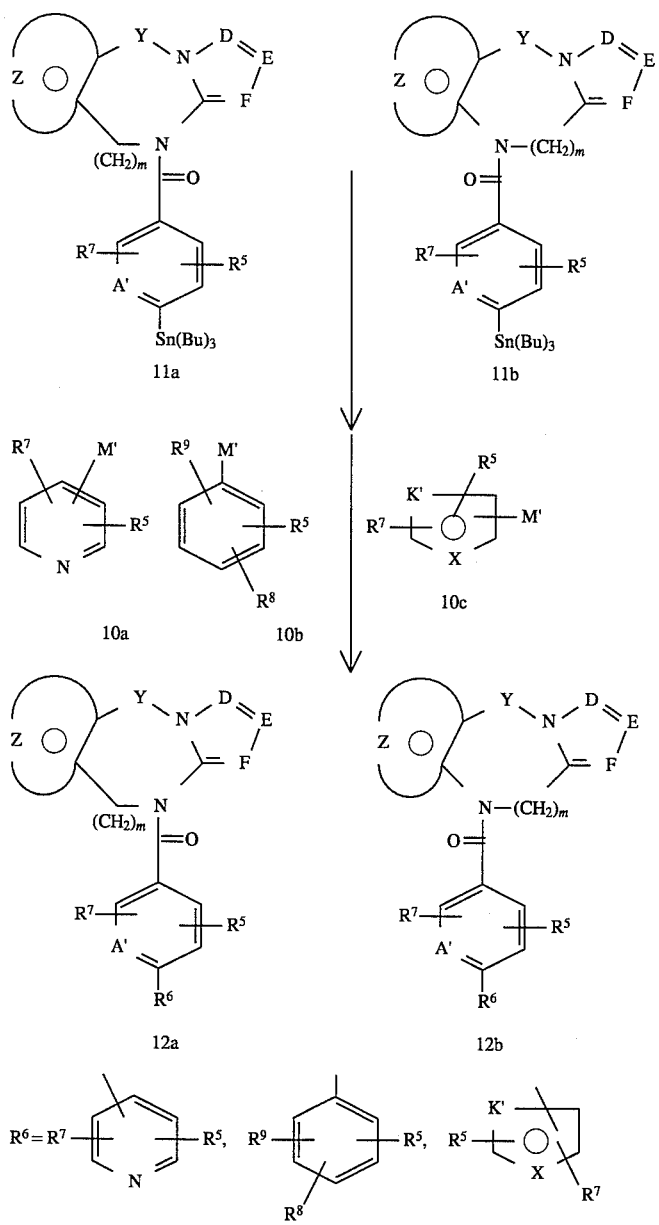

As shown in Scheme IV, coupling of bromo derivative 9a and 9b wherein Z, Y, D, E, F, A', $R^5$, $R^7$ and m are hereinbefore defined, with tributyltin derivatives 13a, 13b and 13c wherein $R^5$, $R^7$, $R^8$, $R^9$, K' and X are hereinbefore defined affords derivatives 14a and 14b where the linking unit between the two aromatic rings is a methylene (—$CH_2$—) group. The tributyltin derivatives 13a, 13b and 13c are prepared by standard procedures described in the literature.

SCHEME IV
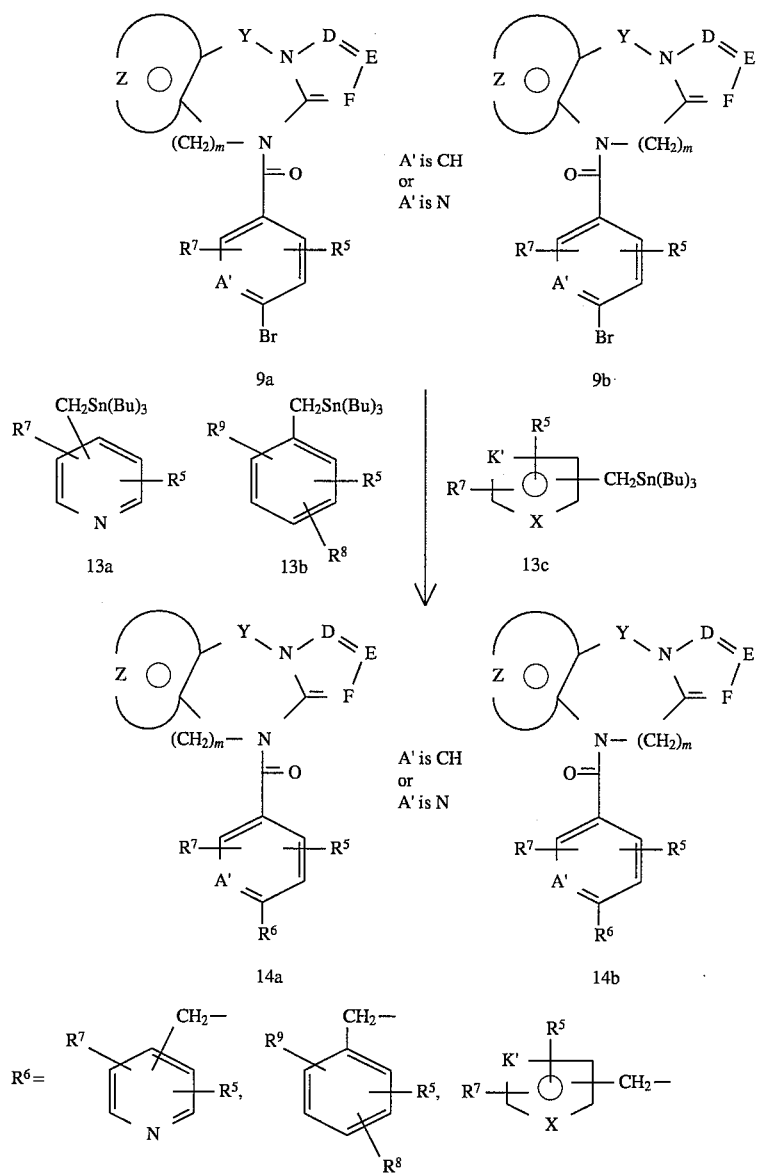
Alternatively, derivatives of structural type 14a and 14b may be prepared by coupling tributyltin derivatives of formulae 11a and 11b with either bromomethyl or iodomethyl derivatives of formulae 15a, 15b and 15c wherein $R^5$, $R^7$, $R^8$, $R^9$, X and K' are hereinbefore defined and M' is I or Br, as shown in Scheme V.

SCHEME V
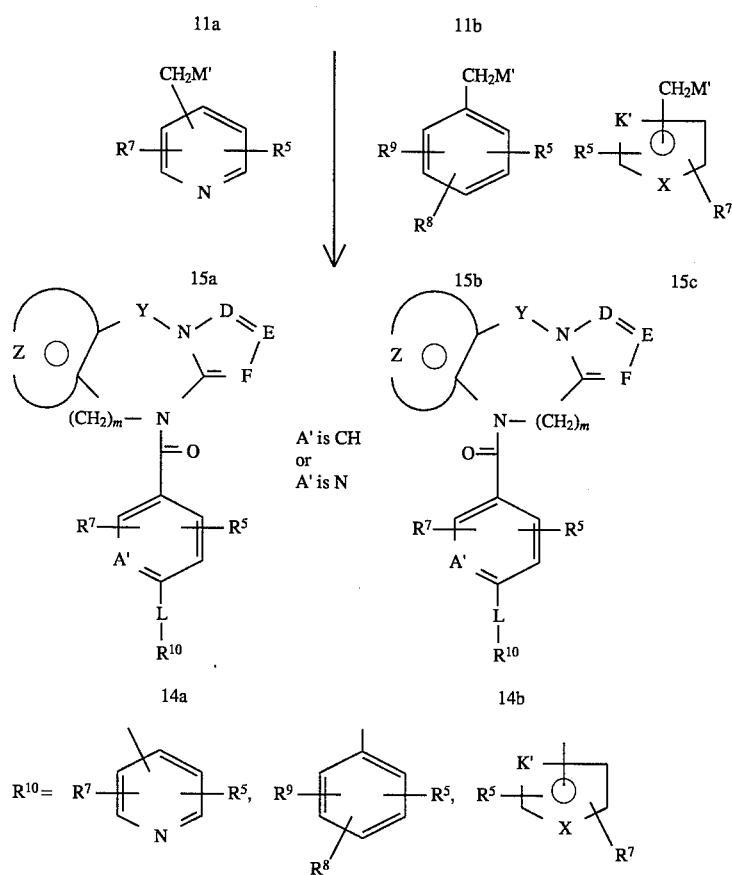
Tributyltin compounds 13a, 13b and 13c wherein L is —CH$_2$— and K', X, R$^5$, R$^7$, R$^8$ and R$^9$ are hereinbefore defined are prepared by reaction of tributyltin hydride with butyl lithium followed by reaction with bromomethyl derivatives 15a, 15b or 15c wherein M' is bromine as shown in Scheme VI.
SCHEME VI
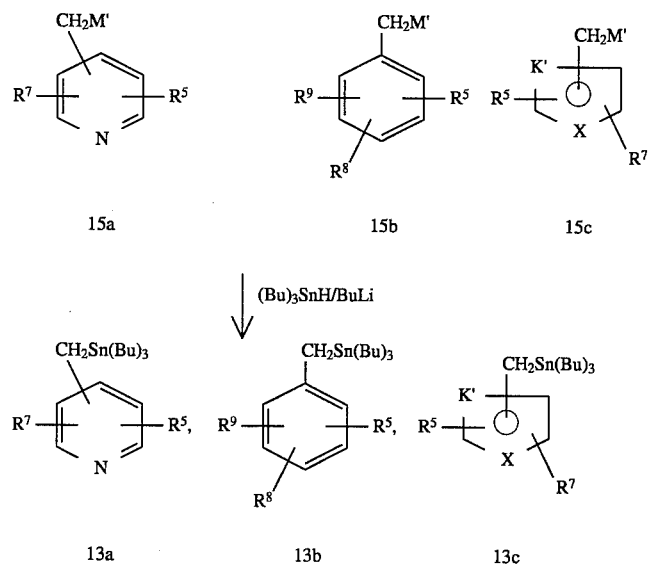

Compounds 17a and 17b of this invention wherein L is O, S, SO, SO$_2$, CO or —CH$_2$— are preferably prepared by reaction of the tricyclic diazepines 3a or 3b with preformed carboxylic acid units of formula 16a preferably activated by formation of the acid chlorides 16b (Scheme VII).

wherein R$^5$, R$^7$ and A' are hereinbefore defined and R$^6$ is selected from

SCHEME VII

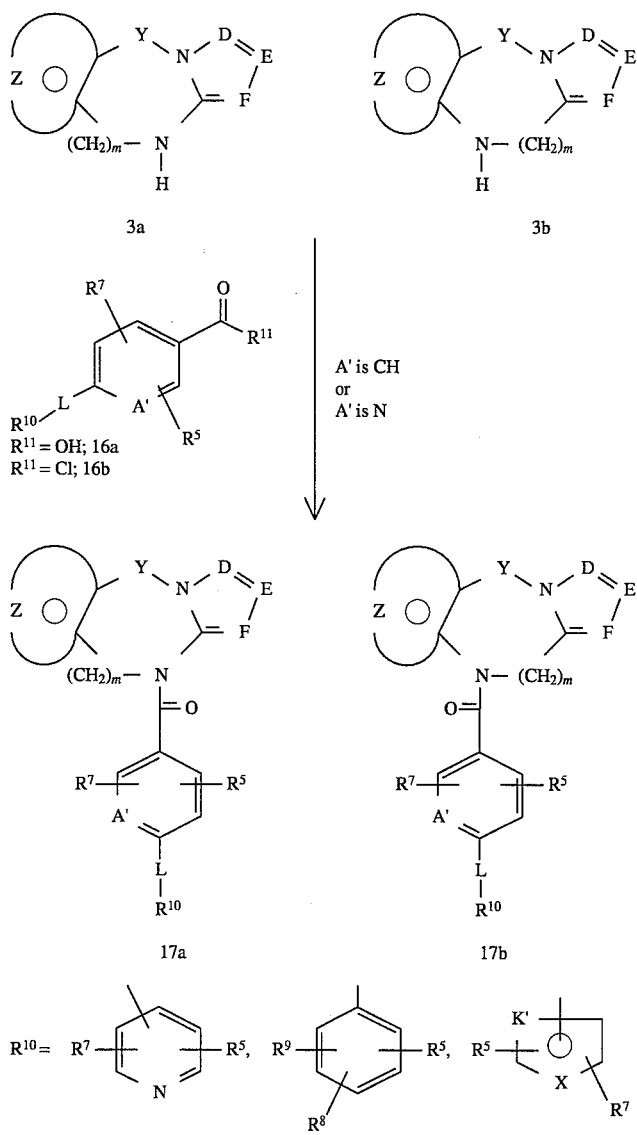

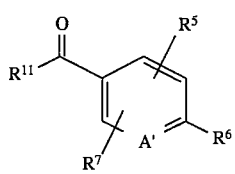

18a: R$^{11}$ = OH
18b: R$^{11}$ = Cl
A' is CH or N

Preformed carboxylic acid units of formula 18a preferably activated by formation of the acid chloride 18b and having the formula

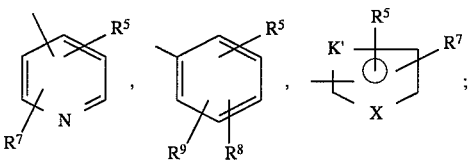

wherein K', X, R$^5$, R$^7$, R$^8$ and R$^9$ are hereinbefore defined are synthesized as shown in Scheme VIII by reaction of 19 where R$^{12}$ is an appropriate removeable carboxylic acid blocking group (alkyl and benzyl) with tributyl tin compounds 8a, 8b, and 8c in the presence of Pd(O) to give intermediate 20.

Bromination of 21 wherein $R^5$, $R^7$ and $R^{12}$ are hereinbefore defined, with N-bromosuccinimide in the presence of ultraviolet light gives bromo intermediate 22 which is coupled with 8a, 8b and 8c in the presence of Pd(O) to give intermediates 23 wherein A' is CH or N as previously defined.

Additional intermediates necessary for coupling to tricyclic derivatives 3a and 3b wherein Z, Y, D, E, F, and m hereinbefore defined and having the formula 25 wherein $R^5$, $R^6$, $R^7$, $R^8$, $R^9$ and $R^{12}$ are hereinbefore defined and L is —C≡C— are synthesized as shown in Scheme X.

Acetylene intermediates 26a, 26b and 26c wherein $R^5$, $R^7$, $R^8$ and $R^9$ are hereinbefore defined, prepared from the corresponding aldehyde by reaction with carbon tetrabromide, and triphenylphosphine in methylene chloride followed by butyl lithium are reacted with iodo intermediate 24 wherein $R^5$, $R^7$ and $R^{12}$ are hereinbefore defined in the presence of palladium (O) to give 26a, 26b, 26c, where L is —C≡C—.

Further intermediates for coupling to tricyclic derivatives 3a and 3b where L is O or S and wherein Z, Y, D, E, F, and m are hereinbefore defined and having the formula 30, 31, and 32 wherein $R^5$, $R^6$, $R^7$ and $R^{12}$ are hereinbefore defined are synthesized as shown in Scheme XI.

of derivative 31 with one mole of 3-chloroperbenzoic acid gives sulfoxide intermediate 32a and reaction with two moles of 3-chloroperbenzoic acid affords the sulfone intermediate 32b.

Other useful intermediates for the preparation of compounds of this invention wherein the connecting atom L is an oxygen atom between aryl-L-heteroaryl, heteroaryl-L-aryl or heteroaryl-1-heteroaryl units as exemplified in formulae 34a, 34b and 37 are prepared as shown in Schemes XII and XIII. The reactions are carried out in inert solvents such as N,N-dimethylformamide, N,N-dimethylacetamide, 1-methyl-2-pyrrolidinone and the like where MH is a metal hydride such as lithium, potassium, and sodium hydride. The

SCHEME XI

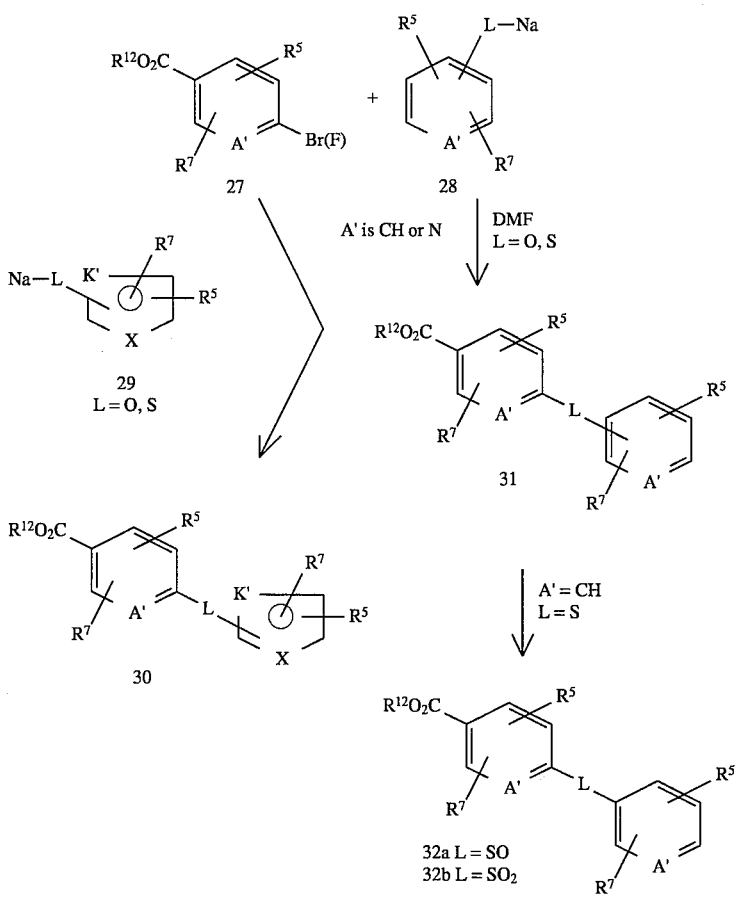

Reaction of 27 wherein A', $R^5$, $R^7$ and $R^{12}$ are hereinbefore defined with sodium salt 28 or 29 in a suitable solvent such as DMF gives intermediates 30 and 31. Further reaction in Schemes XII and XIII may also be carried out by first forming the anions of 33a, 33b and 35 by reaction with an appropriate alkoxide such as potassium t-butoxide.

SCHEME XII
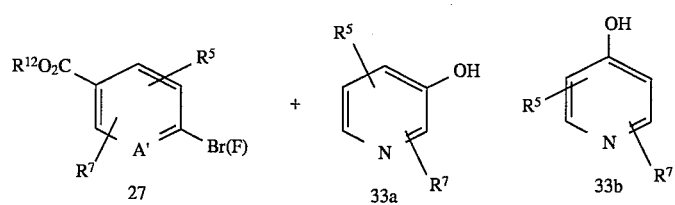
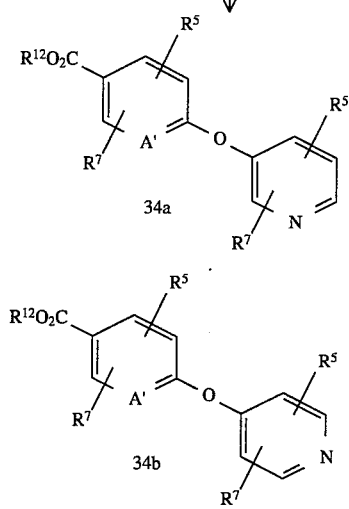
SCHEME XIII
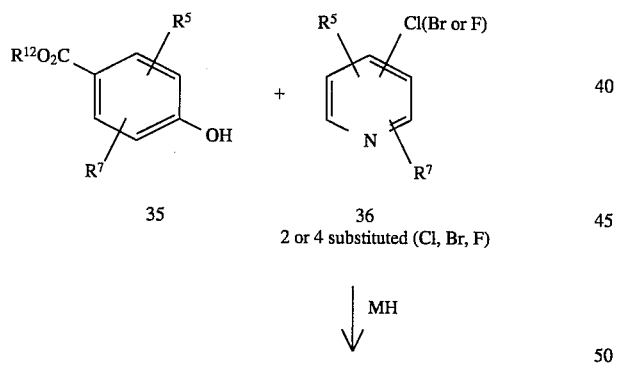
-continued
SCHEME XIII
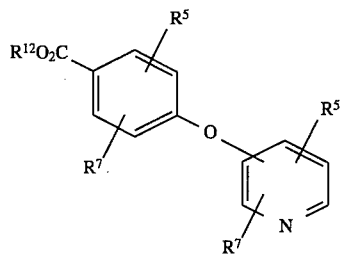
37
2 or 4 substituted

SCHEME XIV

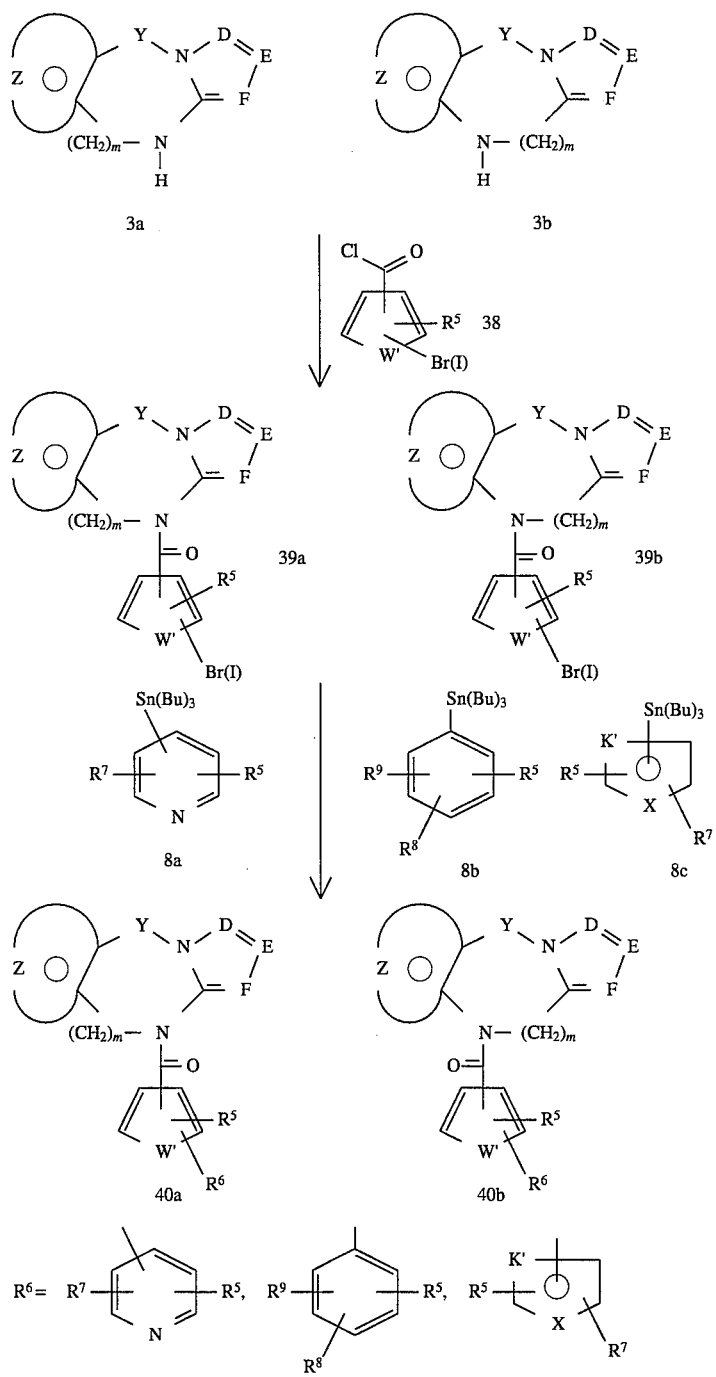

Compounds of this invention may be prepared as shown in Scheme XIV by reaction of tricyclic derivatives of Formula 3a and 3b wherein Z, Y, D, E, F and m are hereinbefore defined, with acid chloride 38 wherein $R^5$ and W' are hereinbefore defined to give intermediates 39a and 39b. Reaction of 39a and 39b with tributyltin derivatives 8a, 8b or 8c where $R^5$, $R^7$, $R^8$, $R^9$, K' and X are hereinbefore defined affords 40a and 40b.

SCHEME XV

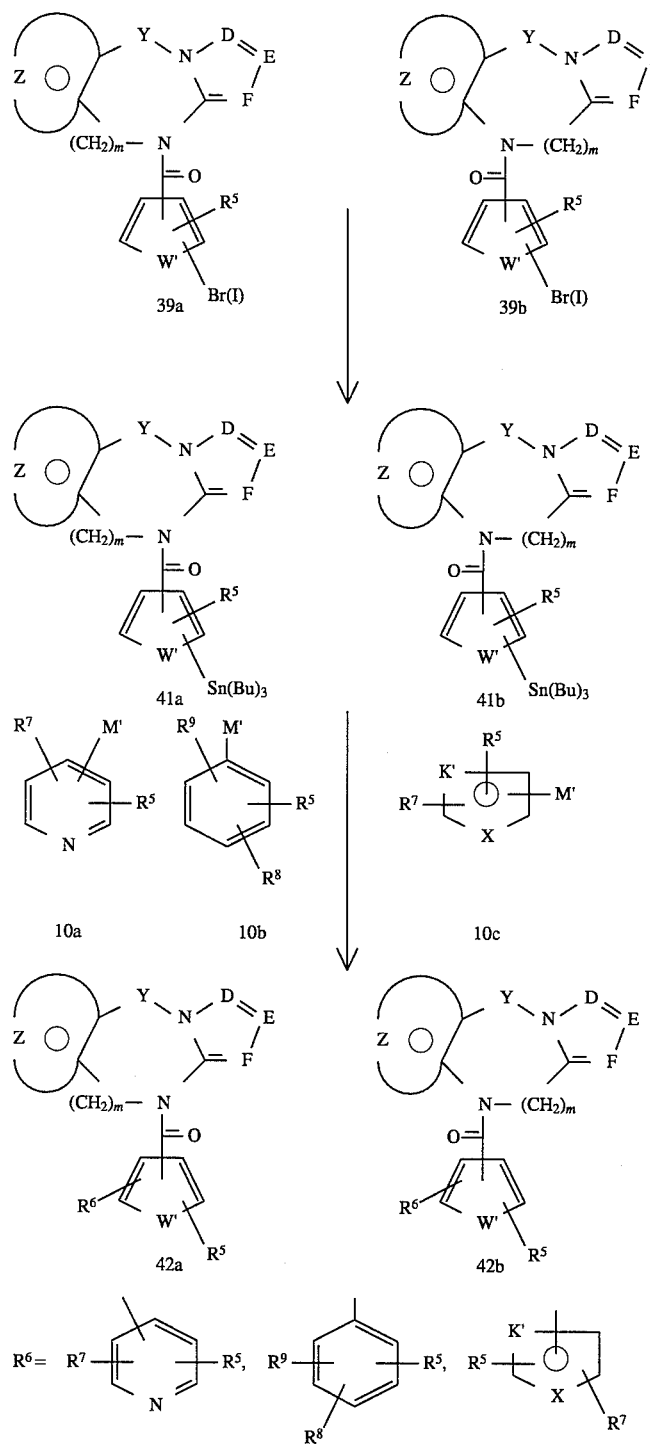

Alternatively, as shown in Scheme XV, the bromo derivates 39a and 39b wherein W', Y, D, E, F, $R^5$, and m are hereinbefore defined are reacted with tetrakis(triphenylphosphine)palladium (O) and bis(tributyltin) in the presence of lithium chloride to give tin intermediate 41a and 41b. Further reaction of the tributyl tin derivatives 41a and 41b with bromo derivatives 10a, 10b or 10c wherein M' is bromo or iodo and K', X, $R^5$, $R^8$ and $R^9$ are hereinbefore defined, in the presence of tetrakistriphenylphosphine palladium (O) gives 42a and 42b.

SCHEME XVI

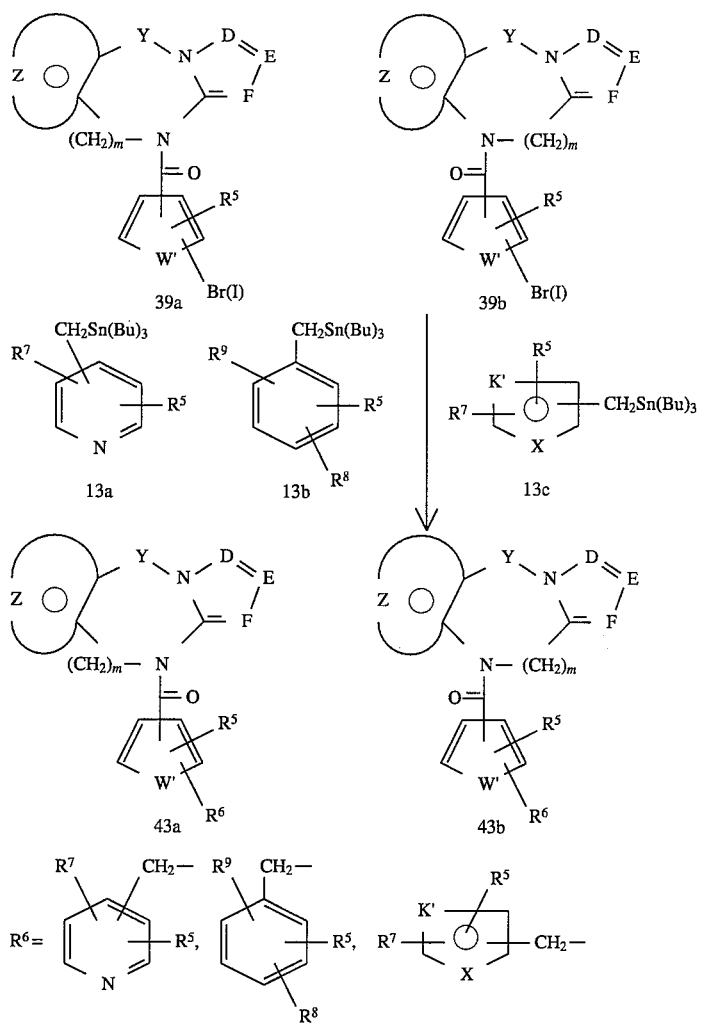

As shown in Scheme XVI, coupling of bromo derivative 39a and 39b with tributyltin derivatives 13a, 13b and 13c affords derivatives 43a and 43b where the linking unit between the two aromatic rings is a methylene (—CH$_2$—) group. The tributyltin derivatives 13a, 13b and 13c are prepared by standard procedures described in the literature.

SCHEME XVII

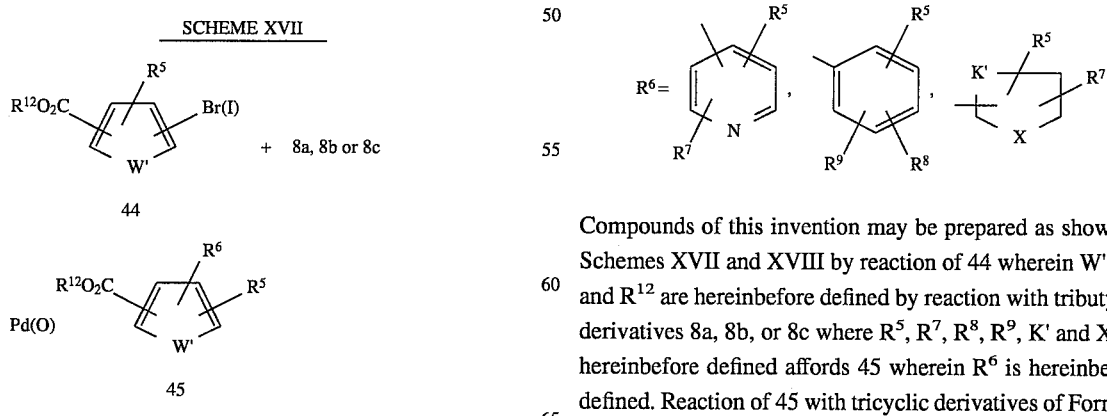

Compounds of this invention may be prepared as shown in Schemes XVII and XVIII by reaction of 44 wherein W', R$^5$, and R$^{12}$ are hereinbefore defined by reaction with tributyltin derivatives 8a, 8b, or 8c where R$^5$, R$^7$, R$^8$, R$^9$, K' and X are hereinbefore defined affords 45 wherein R$^6$ is hereinbefore defined. Reaction of 45 with tricyclic derivatives of Formula 3a and 3b wherein Z, Y, D, E, F and m are hereinbefore defined affords 46a and 46b.

SCHEME XVIII
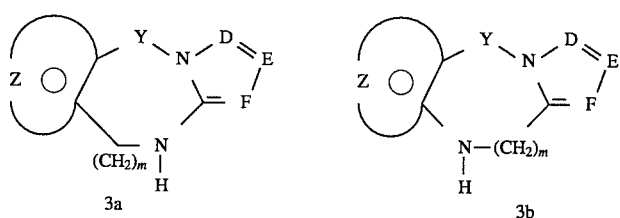
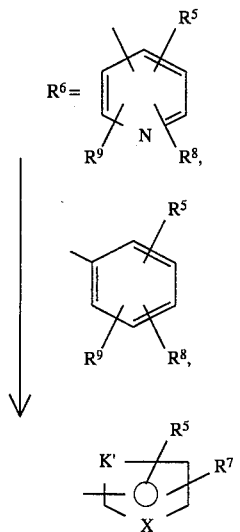
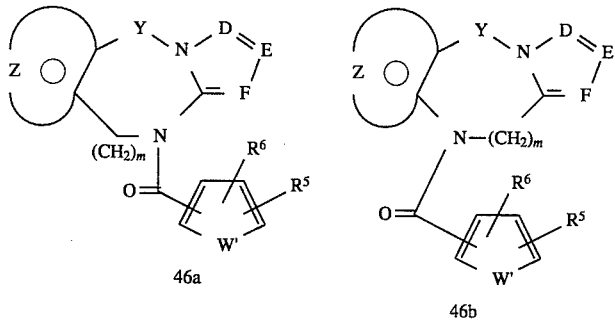
SCHEME XIX
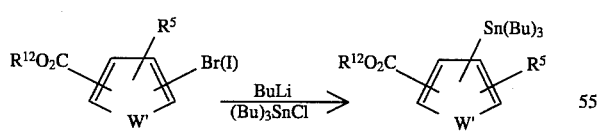
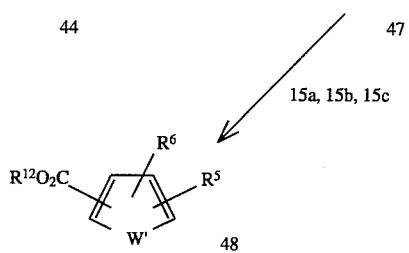
-continued
SCHEME XIX
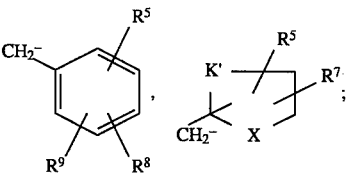

SCHEME XX

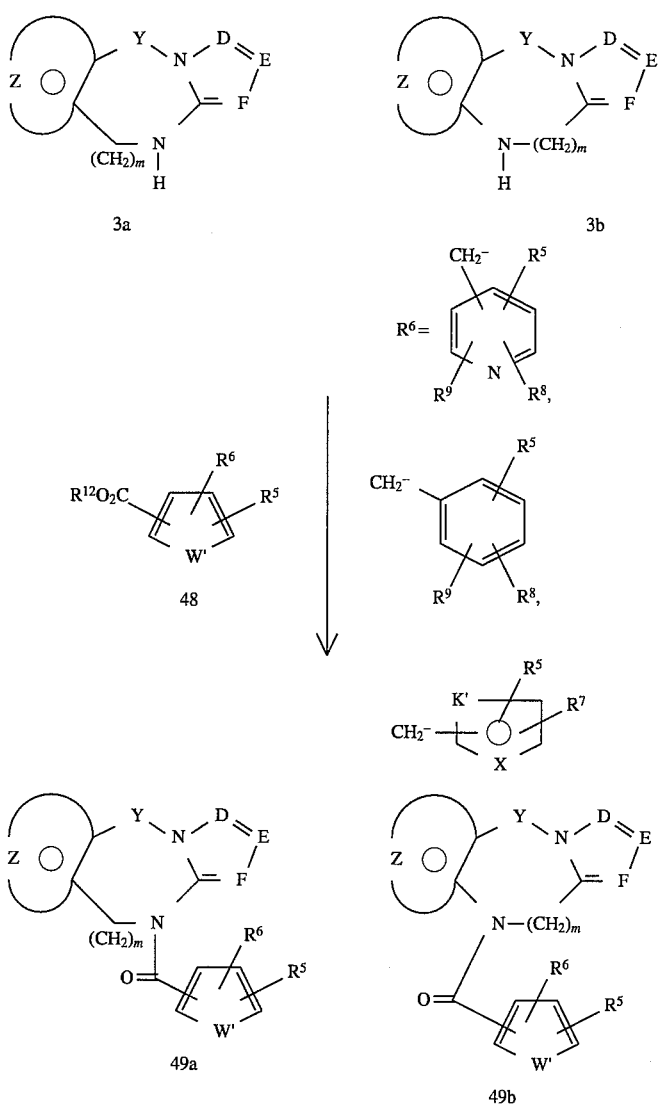

Compounds of this invention may be prepared as shown in Schemes XIX and XX. Reaction of 44 wherein W', $R^5$ are hereinbefore defined and $R^{12}$ is hereinbefore defined with butyl lithium and tributyltin chloride affords 47 which is reacted with derivatives 15a, 15b, or 15c where $R^5$, $R^7$, $R^8$, $R^9$, K', X and M' are hereinbefore defined affords 48 wherein $R^6$ is defined. Reaction of 48 with tricyclic derivatives of Formula 3a and 3b wherein Z, Y, D, E, F and m are hereinbefore defined affords 49a and 49b.

Reference Example 1

10,11-Dihydro-10-(4-iodobenzoyl)-5H-pyrrolo [2,1-c][1,4]benzodiazepine

To a stirred solution of 1.8 g of 10,11 -dihydro-5H-pyrrolo [2,1-c][1,4]benzodiazepine and 3 ml of triethylamine in 100 ml of methylene chloride at 0° C. is added a solution of 2.8 g of 4-iodobenzoyl chloride in 25 ml of methylene chloride. The reaction mixture is stirred at room temperature for 4 hours and evaporated in vacuo to a residue which is partitioned between water and chloroform. The organic layer is dried over $Na_2SO_4$, filtered and evaporated in vacuo to a brown residue which is crystallized from ether-hexane to give 3.0 g of the desired product. Mass spectrum: M+H:323.

Reference Example 2

10,11-Dihydro-10-[4-(tributylstannyl)benzoyl]-5 H-pyrrolo[2,1-c][1,4]benzodiazepine A mixture of 4.1 g of 10,11-dihydro-10-(4 -iodobenzoyl)-5H-pyrrolo[2,1-c][1,4]benzodiazepine, 200 mg of tetrakis(triphenylphosphine)palladium (O), 11.6 g of bis(tributyl) tin and 4.0 g of lithium chloride in 100 ml of anhydrous dioxane is refluxed for 24 hours. The reaction mixture is filtered and the residue is washed with dioxane. The combined filtrates are evaporated in vacuo to a residue which is purified by column chromatography on silica gel by elution with 30% ethyl acetate-hexane to give 5.0 g of the desired product as a solid. Mass spectrum: M+H:583.

Reference Example 3

2-(Tributylstannyl)toluene

To a stirred solution of 3.4 g of 2-bromotoluene in 100 ml of dry tetrahydrofuran at −78° C. is slowly added 8 ml of 2.5M butyl lithium in hexane. The reaction mixture is stirred for 30 minutes and 6.5 g of tri-n-butyl tin chloride in 25 ml of tetrahydrofuran added. The reaction mixture is stirred an additional 1 hour, quenched with water and extracted with ether. The ether extract is dried over $Na_2SO_4$, filtered and the filtrate evaporated in vacuo to give 7.0 g of a residue. Mass spectrum: M+H:381.

Reference Example 4

1-(2-Nitrophenyl)-1H-pyrrole-2-carboxaldehyde

To a solution of 3.76 g of 1-(2-nitrophenyl)pyrrole in 20 ml of N,N-dimethylformamide at 0° C. is added dropwise with stirring 3 ml of phosphorus oxychloride. Stirring is continued for 30 minutes and the reaction mixture is heated at 90° C. for 1 hour. After cooling to room temperature the mixture is treated with crushed ice and the pH adjusted to 12 with 2N sodium hydroxide. The resulting suspension is filtered, washed with water and dried to give 5.81 g of the desired product as a light yellow solid m.p. 119°–122° C.

Reference Example 5

4,5-Dihydro-pyrrolo-[1,2-a]-quinoxaline

To a solution of 1.0 g of 1-(2-nitrophenyl)- 1H-pyrrole-2-carboxaldehyde in 40 ml of ethyl alcohol and 40 ml of ethyl acetate, under argon, is added 40 mg of 10% Pd/C. The mixture is hydrogenated at 40 psi for 2 hours and filtered through diatomaceous earth. The filtrate is concentrated in vacuo to a residue which is dissolved in ether and treated with hexanes to give 0.35 g of the desired product as a beige solid m.p. 108°–110° C.

Reference Example 6

N-(2-Nitrobenzoyl)pyrrole-2-carboxaldehyde

To an ice bath cooled solution of 5.6 g of 2-pyrrolecarboxaldehyde in 40 ml of tetrahydrofuran is added 2.4 g of 60% sodium hydride in mineral oil. The temperature elevates to 40° C. After stirring for 20 minutes a solution of 11.0 g of 2-nitrobenzoyl chloride in 20 ml of tetrahydrofuran is added dropwise for 20 minutes. After stirring in the cold for 45 minutes, the reaction mixture is poured into ice water and ether then filtered. The cake is washed with additional ether. The two phase filtrate is separated and the ether layer dried and concentrated in vacuo to give 10 g of a residue as a dark syrup which is scratched with ethanol to give crystals which are collected by filtration, washed with ether and then dried to afford 3.2 g of solid, m.p. 95°–99° C.

Reference Example 7

10,11-Dihydro-5H-pyrrolo[2,1-c][1,4]benzodiazepin-5-one

A mixture of 1.5 g of N-(2-nitrobenzoyl)pyrrole-2-carboxaldehyde in 50 ml of ethyl acetate, 2 drops of concentrated HCl and 0.3 g of 10% Pd/C is shaken in a Parr apparatus under hydrogen pressure for 2 hours. The reaction mixture is filtered through diatomaceous earth and the filtrate concentrated in vacuo to give 1.0 g of a yellow oil. The residue is purified on thick layer chromatography plates by elution with 4:1 ethyl acetate:hexane to give 107 mg of the desired product as an oily solid.

Reference Example 8

1-(2-Nitrobenzyl)-2-pyrrolecarboxaldehyde

To 5.56 g of 60% sodium hydride in mineral oil, washed three times with hexane, is added 300 ml of N,N-dimethylformamide under argon. The reaction mixture is cooled in an ice-bath and 13.2 g of pyrrole-2-carboxaldehyde is added slowly. The reaction mixture becomes a complete solution and is stirred for an additional 10 minutes. While stirring, 30.0 g of 2-nitrobenzyl bromide is added slowly. After complete addition, the reaction mixture is stirred for 30 minutes, the ice bath is removed and the reaction mixture stirred at room temperature for 24 hours. The N,N-dimethylformamide is concentrated in vacuo to give a residue which is stirred with ice water for 1 hour. The resulting solid is collected, air dried, then vacuum dried to give 30.64 g of the desired product as a tan solid, m.p. 128°–132° C.

Reference Example 9

10,11-Dihydro-5H-pyrrolo[2,1-c][1,4]benzodiazepine

A mixture of 30.6 g of 1-(2-nitrobenzyl)-2-pyrrolecarboxaldehyde and 3.06 g of 10% Pd/C in 400 ml of ethyl acetate and 400 ml of ethyl alcohol is hydrogenated over 18 hours. The reaction mixture is filtered through diatomaceous earth and the filtrate is treated with activated carbon and filtered through diatomaceous earth. The filtrate is concentrated in vacuo to give a residue which is dissolved in methylene chloride containing ethyl alcohol. The solution is passed through a pad of silica gel and the pad washed with a 7:1 hexane-ethyl acetate solution to give 16.31 g of the desired product as solid, m.p. 145°–148° C.

Reference Example 10

1-(o-Nitrobenzyl)-imidazole-2-carboxaldehyde

A 2.0 g portion of sodium hydride (60% in oil) is washed with pentane two times. To the residue is added 110 ml of N,N-dimethylformamide under argon. With stirring and external cooling, 4.80 g of 2-imidazolecarboxaldehyde is added and the cooling bath removed. Slight external heating results in a yellow solution. The reaction mixture is chilled in ice and 10.8 g of 2-nitrobenzyl bromide is added. The reaction mixture is stirred at 0° C. for 18 hours. The volatiles are remove in vacuo to a residue which is stirred with ice water, filtered and the cake washed well with water and suction dried to give 10.9 g of the desired product as a solid, m.p. 141°–144° C. MH+232.

Reference Example 11

10,11-Dihydro-5H-imidazo[2,1-c][1,4]benzodiazepine

A 5.0 g sample of 1-(o-nitrobenzyl)-imidazole-2-carboxaldehyde is dissolved in 150 ml of hot ethyl alcohol, cooled to room temperature and filtered. To the filtrate is added 0.5 g of 10% Pd/C and the mixture hydrogenated at 48 psi for 4 hours. An additional 0.5 g of 10% Pd/C is added and hydrogenation continued for 25 hours at 65 psi. The mixture is filtered through diatomaceous earth and the cake washed with ethyl acetate. The filtrate is evaporated in vacuo to a residue which is dissolved in methylene chloride, treated with activated carbon, filtered through diatomaceous earth and hexanes added to the filtrate at the boil to give 1.86 g of the desired product as a crystalling solid, m.p. 164°–170° C.

Reference Example 12

10,11-Dihydro-5H-imidazo[2,1-c][1,4]benzodiazepine

To a suspension of 4 mmol of lithium aluminum hydride in 20 ml of anhydrous tetrahydrofuran is added a 1 mmol solution of 10,11-dihydro-11-oxo-5H-imidazo[2,1 -c][1,4] benzodiazepine and the mixture is refluxed for 24 hours and cooled at 0° C. To the mixture is added dropwise 0.12 ml of water and 6 ml of 1N sodium hydroxide. The mixture is extracted with ethyl acetate and the solvent removed to give the desired product as a solid. Recrystallization from methylene chloride-hexane gives crystals, m.p. 164°–170° C.

Reference Example 13

10-[(6-Bromo-3-pyridinyl)carbonyl]-10,11-dihydro-5 H-pyrrolo[2,1-c][1,4]benzodiazepine To a solution of 1.0 g of 10,11-dihydro-5 H-pyrrolo[2,1-c][1,4]benzodiazepine and 10 ml of triethylamine in 50 ml of dichloromethane under argon is added 3 g of 6-bromopyridine-3-carbonyl bromide. The mixture is stirred at room temperature for 16 hours and then poured into 100 ml of water. The organic layer is separated and washed with 2% HCl, water, saturated $NaHCO_3$ and dried ($Na_2SO_4$), the solvent removed under vacuum and the residue chromatographed on silica gel with ethyl acetate-hexane as solvent to give the product as a solid.

Reference Example 14

9,10-Dihydro-4H-furo[2,3-e]pyrrolo[1,2-a][1,4] diazepine

To a suspension of 4 mmol of lithium aluminum hydride in 25 ml of anhydrous tetrahydrofuran is added 1 mmol of 9,10-dihydro-4H-furo[2,3-e]pyrrolo[1,2 -a][1,4]diazepin-9-one. The mixture is refluxed for 12 hours and allowed to stand overnight. To the mixture is added dropwise 0.12 ml of water and then 6 ml of 1N sodium hydroxide. The mixture is extracted with ethyl acetate and the extract dried ($Na_2SO_4$). The volatiles are removed in vacuo to give the desired product as a solid.

Reference Example 15

9,10-Dihydro-4H-furo[2,3-e]pyrrolo[1,2-a][1,4] diazepine

A solution of 1 mmol of 4H-furo[2,3-e]pyrrolo[1,2-a][1,4]diazepine and 0.2 g if 10% Pd/C in 10 ml of ethanol is hydrogenated for 18 hours. The reaction mixture is filtered through diatomaceous earth and the filtrate is evaporated in vacuo to give the desired product as a solid.

Reference Example 16

10-[(6-Iodo-3-pyridinyl)carbonyl]-10,11-dihydro-5 H-pyrrolo[2,1-c][1,4]benzodiazepine To a solution of 1.0 g of 10,11-dihydro-5 H-pyrrolo[2,1-c][1,4]benzodiazepine and 10 ml of triethylamine in 50 ml of dichloromethane under argon is added 3.2 g of 6-iodopyridine-3-carbonyl chloride. The mixture is stirred at room temperature for 16 hours and then poured into 100 ml of water. The organic layer is separated and washed with 2% HCl, water, saturated $NaHCO_3$ and dried ($Na_2SO_4$). The solvent is removed under vacuum and the residue chromatographed on silica gel with ethyl acetate-hexane as solvent to give the product as a solid.

Reference Example 17

9,10-Dihydro-4H-pyrrolo[1,2-a]thieno[2,3-e] [1,4]diazepine

To a mixture of 7.0 g of 9-oxo-9,10-dihydro- 4H-pyrrolo [1,2-a]thieno[2,3-e][1,4]diazepin in 25 ml of anhydrous tetrahydrofuran is added 9 ml of 10 molar boron-dimethylsulfide in tetrahydrofuran. The mixture is refluxed for 6 hours. The solution is cooled to room temperature and 25 ml of methanol added dropwise. The volatiles are removed under vacuum. To the residue is added 100 ml of 2N NaOH. The mixture is refluxed 5 hours and filtered. The solid is extracted with dichloromethane and the extract is washed with 2N citric acid, water and dried ($Na_2SO_4$). The solvent is removed in vacuo to give the desired product as a solid.

Reference Example 18

4,10-Dihydro-5H-pyrrolo[1,2-a]thieno[3,2-e][1,4] diazepine

To a suspension of 7.0 g of 5-oxo-4,5 -dihydropyrrolo[1, 2-a]thieno[3,2-e][1,4]diazepine in 25 ml of anhydrous tetrahydrofuran is added 9 ml of 10M borane-dimethylsulfide in tetrahydrofuran. The mixture is refluxed for 6 hours. The solution is cooled to room temperature and 25 ml of methanol added dropwise. The volatiles are removed under vacuum. To the residue is added 100 ml of 2N NaOH. The mixture is refluxed 5 hours and filtered. The solid is extracted with dichloromethane and the extract is washed with 2N citric acid, water and dried ($Na_2SO_4$). The solvent is removed to give a solid.

Reference Example 19

5,6-Dihydro-4H-[1,2,4]triazolo[4,3-a][1,5] benzodiazepine

A mixture of 7.0 g of 5,6-dihydro-4H-[1,2,4] -triazolo-[4,3-a][1,5]benzodiazepin-5-one in 25 ml of tetrahydrofuran is added 9 ml of 10M boranedimethylsulfide in tetrahydrofuran. The mixture is refluxed for 6 hours, cooled to room temperature and 25 ml of methanol added dropwise. The volatiles are removed under vacuum and to the residue is added 100 ml of 2N sodium hydroxide. The mixture is refluxed for 5 hours, chilled and extracted with dichloromethane. The extract is washed with 2N citric acid, water and dried ($Na_2SO_4$). The solvent is removed under vacuum to give a solid. The solid is purified by chromatography on silica gel to give the desired product.

Reference Example 20

1-(2-Nitrophenyl)-1H-pyrrole-2-carboxaldehyde

A sample of 4.7 g of sodium hydride (60% in oil) is washed with hexane (under argon). To the sodium hydride is added 200 ml of dry N,N-dimethylformamide and the mixture is chilled to 0° C. To the mixture is added 10.11 g of pyrrole-2-carboxaldehyde in small portions. The mixture is stirred 10 minutes and 15.0 g of 1 -fluoro-2-nitrobenzene added dropwise. After the addition, the mixture is stirred at room temperature 16 hours and the mixture concentrated (65° C.) under high vacuum. To the residue is added 400 ml of dichloromethane and the mixture washed with 150 ml each of $H_2O$, brine and dried ($Na_2SO_4$). The solvent is removed in vacuo to give a yellow solid. Crystallization from ethyl acetate-hexane (9:1) gives 17.0 g of light yellow crystals, m.p. 119°–122° C.

Reference Example 21

4,10-Dihydro-5H-pyrrolo[1,2-a]thieno[3,2-e] [1,4]diazepine

To an ice cooled mixture of 2.1 g of pyrrole- 2-carboxylic acid and 3.2 g of methyl 3-amino-thiophene- 2-carboxylate in 40 ml of dry dichloromethane is added 4 g of N,N-dicyclohexylcarbodiimide. The mixture is stirred at room temperature 3 hours and filtered. The filter cake is washed with dichloromethane and then extracted twice with 60 ml of acetone. The acetone extract is concentrated tdo dryness to give 0.8 g of solid, m.p. 214°–218° C. To a suspension of the preceding compound (1.19 g) in 20 ml of dry tetrahydrofuran is added 0.2 g of sodium hydride (60% in oil). After the hydrogen evolution, the mixture is stirred and refluxed for 4.5 hours, cooled and poured into ice-water. The precipitated solid is filtered and the solid triturated with petroleum ether (bp 30°–60° C.) to give 0.75 g of 4,10-dihydro-4,10-dioxo-5H-pyrrolo[1,2-a]thieno[3,2 -e][1,4]diazepine as a solid, m.p. 280°–290° C. The preceding compound (0.362 g) is added to an ice-water cooled solution of 1M diborane in tetrahydrofuran. The mixture is stirred at room temperature for 65 hours. The solution is concentrated to dryness and ice-water added to the residue. The mixture is acidified with dilute HCl, stirred and then basified with solid $NaHCO_3$. The mixture is filtered to give 0.223 g of a solid (foam) m.p. 80°–85° C.

Reference Example 22

10,11-Dihydro-5H-1,2,4-triazolo[3,4-c][1,4]-benzodiazepine

A mixture of 2.2 g of 2-cyanoaniline, 2.0 g of methyl bromoacetate and 1.3 g of potassium carbonate in 12 ml of dry N,N-dimethylformamide is heated at 150°–155° C. for 40 minutes. The cooled mixture is poured into ice-water and the mixture filtered to give 2 g of methyl [N-(2-cyanophenyl)amino]acetate as a yellow solid, m.p. 70°–78° C. The preceding compound (2.0 g) is added to a solution of 0.5 g of sodium methoxide in 50 ml of methanol. The mixture is shaken under an atmosphere of hydrogen with the catalyst Raney-Ni for 19 hours. The mixture is filtered through diatomaceous earth and the filtrate evaporated. Water is added to the residue and the mixture filtered to give 2,3,4, 5-tetrahydro-1H-1,4 -benzodiazepin-3-one as a yellow solid, m.p. 167°–170° C.

A mixture of the preceding compound (1.6 g) and 0.84 g of phosphorus pentasulfide in 10 ml of dry (dried over KOH) pyridine is stirred and heated at 80°–85° C. for 15 minutes. The mixture is poured into water and stirred for 30 minutes. Filtration gives 1.0 g of 1,2,4,5-tetrahydro-3H-1,4-benzodiazepin-3-thione as yellow solid, m.p. 150°–153° C.

The preceding compound (0.5 g) and 0.5 g of N-formylhydrazine in 6 ml of dry n-butanol is refluxed for 16 hours and the solvent removed. The gummy residue is triturated with cold water and the mixture filtered. The solid is triturated with acetone to give 0.19 g of yellow solid, m.p. 232°–237° C.

Reference Example 23

4,5-Dihydro-6H-[1,2,4]triazolo[4,3-a][1,5]-benzodiazepine

A mixture of 2,3,4,5-tetrahydro-1H-1,5 -benzodiazepin-2-thione (0.8 g) and 0.80 g of N-formylhydrazine in 8 ml of n-butanol is stirred and refluxed for 18 hours and the solvent removed under vacuum. Ice water is added to the residual solid and the mixture filtered to give 0.312 g of a gray solid, m.p. 162°–165° C.

Reference Example 24

4,5-Dihydro-6H-imidazo[1,2-a][1,5]benzodiazepine

A mixture of 30 g of acrylic acid, 33 g of o-phenylenediamine is heated on a steam bath for 1.5 hours and the cooled black mixture triturated with ice-water. The aqueous phase is decanted and ice and aqueous ammonium hydroxide added to the residue. The mixture is extracted with dichloromethane and the extract concentrated to dryness. The residue is triturated with carbon tetrachloride and filtered. The oily solid is triturated with a small amount of ethanol to give 9.7 g of a solid. Trituration of the solid with ethyl acetate gives 2,3,4,5-tetrahydro-1H-1,5-benzodiazepine-2-one as an impure solid, m.p. 75°–107° C.

A mixture of the preceding compound (11.3 g) and 5.9 g of phosphorus pentasulfide in 70 ml of dry pyridine is stirred and heated at approximately 80° C. for 20 minutes. The mixture is poured into water and the mixture stirred for 30 minutes. Filtration gives 8.6 g of 2,3,4,5-tetrahydro-1H-1, 5-benzodiazepin-2-thione as a solid, m.p. 154°–157° C.

A mixture of the preceding compound (0.70 g), 1.0 g of aminoacetaldehyde dimethyl acetal and 15 mg of 4-methylbenzenesulfonic acid monohydrate in 6 ml of dry n-butanol is refluxed for 4 hours and the solvent removed under vacuum. The residue is heated (refluxed) with 10 ml of 3N hydrochloric acid for 55 minutes. Ice is added to the cooled mixture and the mixture made basic with solid $NaHCO_3$. The mixture is extracted with dichloromethane and the extract dried ($Na_2SO_4$). The solvent is removed to give an orange syrup which solidified on standing. The oily solid is triturated with acetone to give a light yellow solid (0.185 g) m.p. 119°–122° C.

Reference Example 25

1-(2-Nitrophenyl)-2-pyrroleacetic acid, ethyl ester

To a stirred mixture of 1.88 g of 1-(2 -nitrophenyl)pyrrole, 4.80 g of ethyl iodoacetate and 2.22 g of $FeSO_4.7H_2O$ in 40 ml of dimethyl sulfoxide is added dropwise 10 ml of 30% hydrogen peroxide while keeping the reaction mixture at room temperature with a cold water bath. The mixture is stirred at room temperature for one day. An additional 2.4 g of ethyl iodoacetate, 1.1 g of $FeSO_4.7H_2O$ and 5 ml of 30% hydrogen peroxide is added and the mixture stirred at room temperature for 1 day. The mixture is diluted with water and extracted with diethyl ether. The organic extract is washed with water, brine and dried ($Na_2SO_4$). The solvent is removed and the residue (2.12 g) chromatographed on silica gel with ethyl acetate-hexane (1:4) as solvent to give 0.30 g of product as a brown gum.

Reference Example 26

6,7-Dihydro-5H-pyrrolo[1,2-a][1,5]benzodiazepin-6-one

To a solution of 0.8 mmol of 1-(2-nitrophenyl)- 2-pyrroleacetic acid, ethyl ester in 3 ml of ethanol is added stannus chloride dihydrate ($SnCl_2.H_2O$) in 2 ml of concentrated hydrochloric acid (with cooling in water bath). The mixture is stirred at room temperature for 5 hours and chilled in an ice bath. To the mixture is added slowly saturated sodium carbonate solution. The solid which precipitates is filtered and the solid washed with water and then extracted with ethyl acetate. The ethyl acetate extract is dried ($Na_2SO_4$) and the solvent removed to give 0.16 g of solid which is triturated with ether to give 0.11 g of product as an off-white solid.

Reference Example 27

6,7-Dihydro-5H-pyrrolo[1,2-a][1,5]benzodiazepine

To a solution of 0.070 g of 6,7-dihydro-5 H-pyrrolo[1,2-a][1,5]benzodiazepin-6-one in 2 ml of tetrahydrofuran is added 0.45 ml of a 2.0M solution of diborane-dimethylsulfide in tetrahydrofuran. The mixture is refluxed for 3 hours, poured into water and made basic with 2N NaOH. The tetrahydrofuran is removed under vacuum and the residual aqueous mixture extracted with diethyl ether. The extract is washed with brine, dried ($Na_2SO_4$) and the solvent removed to give 0.065 g of a colorless oil; one spot by thin layer chromatography (silica gel) with ethyl acetate-hexane (1:2) as solvent (Rf 0.81).

Reference Example 28

1-[2-Nitro-5-(ethoxycarbonyl)benzyl]-pyrrole-2 -carboxaldehyde

To a stirred slurry of 2.2 g of sodium hydride (60% in oil, washed with hexane) in tetrahydrofuran is added at 0° C. a solution of 4.5 g of pyrrole-2 -carboxaldehyde in 25 ml of tetrahydrofuran. After the addition is complete, a solution of 15 g of ethyl 4 -nitro-3-bromomethylbenzoate in 30 ml of dry tetrahydrofuran is slowly added under nitrogen. The reaction mixture is stirred at 20° C. for 8 hours and carefully quenched with water. The reaction mixture is extracted with chloroform which is washed with water, dried with $Na_2SO_4$ and concentrated in vacuo to give 12 g of the desired product as a solid; mass spectrum (M+H) 349.

Reference Example 29

1-[2-Nitro-4-(ethoxycarbonyl)benzyl]-pyrrole-2-carboxaldehyde

The conditions of Reference Example 28 are used with ethyl 3-nitro-4-bromomethylbenzoate to give 13.0 g of the desired product as a solid; mass spectrum (M+H) 349.

Reference Example 30

Ethyl 10,11-Dihydro-5H-pyrrolo[2,1 -c][1,4]benzodiazepine-7-carboxylate

A solution of 10.0 g of 1-[2-nitro-5 -(ethoxycarbonyl)benzyl]-pyrrole-2-carboxaldehyde in 150 ml of absolute ethanol containing 1.0 g of 10% Pd/C is hydrogenated in a Parr apparatus for 16 hours under 40 psi of hydrogen. The reaction mixture is filtered through a pad of diatomaceous earth and the filtrate concentrated in vacuo to a residue of 5.5 g of the desired product as a solid; mass spectrum (M+H)255.

Reference Example 31

Ethyl 10,11-Dihydro-5H-pyrrolo[2,1-c] [1,4]benzodiazepine-8-carboxylate

The hydrogenation conditions of Reference Example 30 are used with 1-[2-nitro-4-(ethoxycarbonyl)benzyl]-pyrrole-2-carboxaldehyde to give 5.0 g of the desired product as a solid; mass spectrum (M+H)255.

Reference Example 32

4-[(4-Methylphenyl)thio]benzoic Acid

A mixture of 6.0 g of 4-mercapto-toluene and 9.2 g of potassium t-butoxide is stirred at room temperature under a nitrogen atmosphere in 50 ml of dimethylsulfoxide for 10 minutes followed by the addition of 11.5 g of 4-bromobenzoic acid and 0.2 g of copper metal. The reaction mixture is stirred at 210° C. for 16 hours. The reaction mixture is poured over crushed ice and filtered through diatomaceous earth. The filtrate is acidified with HCl until pH 2. The resulting solid is collected, washed with water and 60 ml of petroleum ether to give 8.5 g of the desired product, m.p. 105°–107° C., M+H=245.

Reference Example 33

4-(Phenylthio)benzoic Acid

The conditions to prepare Reference Example 32 c1384847 are used with 6.0 g of mercaptobenzene, 12.22 g of potassium t-butoxide and 13.15 g of 4-bromobenzoic acid to give 12.0 g of the desired product as a solid, m.p. 101°–103° C.; M+H=231.

Reference Example 34

4-(Phenylthio)benzoyl Chloride

A solution of 2.0 g of Reference Example 33 in 30 ml of thionyl chloride under nitrogen is refluxed for 40 minutes. The volatiles are evaporated in vacuo and the residue evaporated two times with 30 ml of carbon tetrachloride to give the desired product as a residue which is dissolved in 30 ml of methylene chloride and used in the next step.

Reference Example 35

4-[(4-Methylphenyl)thio]benzoyl Chloride

The conditions to prepare Reference Example 34 are used with 2.0 g of Reference Example 32 and 30 ml of thionyl chloride to give 2.16 g of the desired product in a solution of 30 ml of methylene chloride.

Reference Example 36

4-(Benzoyl)benzoyl Chloride

The conditions to prepare Reference Example 34 are used with 2.0 g of 4-benzoylbenzoic acid and 30 ml of thionyl chloride to give the desired product in a solution of 30 ml of methylene chloride.

Reference Example 37

4-[(4-Methylphenyl)sulfonyl]benzoyl Chloride

The conditions to prepare Reference Example 34 are used with 2.0 g of Reference Example 38 and 30 ml of thionyl chloride to give the desired product in a solution of 30 ml of methylene chloride.

Reference Example 38

4-[(4-Methylphenyl)sulfonyl]benzoic Acid

A mixture of 4.0 g of Reference Example 32, 11.3 g of m-chloroperbenzoic acid in 100 ml of chloroform under nitrogen is stirred at reflux for 16 hours. The reaction mixture is poured into water and the organic layer separated, washed with 2N HCl and water. The organic layer is dried ($Na_2SO_4$) and evaporated to dryness in vacuo to give 6.5 g of the desired product as a yellowish oil.

Reference Example 39

4-(Phenylsulfonyl)benzoic Acid

A mixture of 7.0 g of Reference Example 33 and 11.5 g of m-chloroperbenzoic acid in 80 ml of chloroform under nitrogen is stirred at reflux for 16 hours. The reaction mixture is evaporated in vacuo and the residue suspended in 200 ml of ice water. The resulting insoluble solid product is collected and dried in a vacuum oven at 60° C. to give 7.2 g of the desired product, m.p. 128°–132° C. M+H=263.

Reference Example 40

4-[(4-Methylphenyl)sulfonyl]benzoic Acid, Methyl Ester

A solution of 6.5 g of Reference Example 38 in 200 ml of methyl alcohol containing a few drops of sulfuric acid is refluxed for 16 hours. The volatiles are removed in vacuo and 150 ml of ice water added to the residue. The resulting solid is collected by filtration and washed with 200 ml of water. The solid is dried in a vacuum over at 60° C. for 16 hours to give 3.5 g of a white fluffy product. M+H=291.1; M+Na=313.1

Reference Example 41

4-[(4-Methylphenyl)sulfonyl]benzoic Acid

A mixture of 2.5 g of Reference Example 40 is dissolved in 60 ml of 1:1 water:methanol and 20 ml of 5% NaOH and stirred at room temperature for 8 hours. The volatiles are evaporated in vacuo to a residue which is stirred in 50 ml of ice water and acidified with about 20 ml of 10N HCl solution. The resulting solid is collected, washed with 200 ml of water and dried in a vacuum over at 60° C. to give 2.0 g of the desired product, M+H=277.

Reference Example 42

4-[(4-Methylphenyl)sulfonyl]benzoyl Chloride

A mixture of 2.0 g of Reference Example 41 and 30 ml of thionyl chloride is heated at 80° C. under nitrogen for 45 minutes. The volatiles are evaporated in vacuo to a residue which is evaporated with toluene and with carbon tetrachloride. The final residue is dissolved in 30 ml of methylene chloride to be used in the next step.

Reference Example 43

4'-(2-Propenyloxy)-[1,1'-biphenyl]-4-carboxylic Acid Ethyl Ester

A mixture of 10.0 g of 4'-hydroxy-[1,1'-biphenyl]-4-carboxylic acid, ethyl ester is dissolved in 100 ml of acetone and 8.02 g of allyl bromide added under a nitrogen atmosphere. While stirring 15.0 g of potassium carbonate is added and the reaction mixture refluxed for 16 hours. The reaction mixture is cooled to 0° C. and poured into 200 ml of ice-water and extracted with chloroform (3×150 ml). The combined extracts are washed with 1N HCl and water, dried ($Na_2SO_4$) and evaporated in vacuo to give 12.0 g of the desired product m.p. 89°–92° C. M+H=283.

Reference Example 44

4'-(2-Propenyloxy)-[1,1'-biphenyl]-4-carboxylic Acid

A mixture of 6.0 g of Reference Example 43 in 60 ml of ethanol and 30 ml of 5N NaOH is stirred at room temperature for 4 hours. The reaction mixture is poured into 200 ml of ice water, acidified with HCl, extracted with chloroform (3×150 ml), washed with saturated $NaHCO_3$ and water. The organic layer is dried ($Na_2SO_4$) and evaporated in vacuo to give 4.4 g of the desired product as a solid, m.p. 360° C., M+H=255.

Reference Example 45

4'-(2-Propenyloxy)-[1,1'-biphenyl]-4-carbonyl chloride

A mixture of 9.0 g of Reference Example 44 in 45 ml of thionyl chloride is refluxed under nitrogen for 45 minutes. The volatiles are evaporated in vacuo and the residue evaporated in vacuo from carbontetrachloride (2×30 ml) to a residue which is dissolved in 30 ml of methylene chloride for use in the next reaction.

Reference Example 46

Tributyl[2-(trifluoromethyl)phenyl]Stannane

To a solution of 10.0 g of 2-bromotrifluoromethylbenzene under nitrogen in 100 ml of tetrahydrofuran while cooling in a dry ice-acetone bath is added dropwise 30.6 ml of a 1.6M solution of butyl lithium via syringe. Stirring is continued for 1 hour. To the reaction mixture is added dropwise 15.9 g of tributyltin chloride in 30 ml of tetrahydrofuran. Stirred ? additional hours. The reaction mixture is quenched with 20 ml of water and after stirring for 20 minutes, extracted with chloroform (3×100 ml). The organic layer is filtered through diatomaceous earth and the filtrate washed with saturated $NaHCO_3$ and water. The organic layer is dried ($Na_2SO_4$) and evaporated in vacuo to give 16.8 g of the desired product. MS 379.1

Reference Example 47

2-(Tributylstannyl)pyridine

To a solution of 10.0 g of 2-bromo-pyridine under nitrogen in 100 ml of tetrahydrofuran while cooling in a dry ice-acetone bath is added dropwise 47.0 ml of a 1.6M solution of butyl lithium via syringe. Stirring is continued for 1 hour. To the reaction mixture is added dropwise 24.7 g of tributyltin chloride in 30 ml of tetrahydrofuran and stirred 1 additional hour. The reaction mixture is quenched with 20 ml of water and 100 ml additional water is added. After stirring for 20 minutes the reaction mixture is extracted with chloroform (3×100 ml). The organic layer is filtered through diatomaceous earth and the filtrate washed with saturated $NaHCO_3$ and water. The organic layer is dried ($Na_2SO_4$) and evaporated in vacuo to give 21.2 g of the desired product. MS 379.1

Reference Example 48

2-(Tributylstannyl)thiazole

To a solution of 10.0 g of 2-bromothiazole under nitrogen in 50 ml of tetrahydrofuran while cooling in a dry ice-acetone bath is added dropwise 36.6 ml of a 1.6M solution of butyl lithium via syringe. Stirring is continued for 1 hour. To the reaction mixture is added dropwise 29.8 g of tributyltin chloride in 20 ml of tetrahydrofuran. Stirred 1 additional hour. The reaction mixture is quenched with 20 ml of water and 50 ml additional water is added. After stirring for 20 minutes the reaction mixture is extracted with chloroform (3×60 ml). The organic layer is dried ($Na_2SO_4$) and evaporated in vacuo to give 11.7 g of the desired product.

Reference Example 49

10-[(6-Chloro-3-pyridinyl)carbonyl]-10,11-dihydro-5 H-pyrrolo[2,1-c][1,4]benzodiazepine To a solution of 1.0 g of 10,11-dihydro-5 H-pyrrolo[2,1-c][1,4]benzodiazepine in 50 ml of dry methylene chloride, under nitrogen, and 7.0 ml of triethylamine is added 1.43 g of 6-chloro-pyridine-3 -carbonyl chloride. The reaction mixture is stirred at room temperature for 16 hours and poured into 100 ml of water. The organic layer is separated, washed with 2% HCl, water, saturated $NaHCO_3$, and dried ($Na_2SO_4$). The solvent is evaporated An vacuo to give a residue which is columned on silica gel by elution with 7:1 to 1:1 ethyl acetate:hexane to give 1.76 g of the desired product as a yellowish crystalline solid. M+H=324.

Reference Example 50

4,5-Dihydro-4,4-dimethyl-2-(2-thienyl)-oxazole

A solution of 30.4 g of 2-amino-2-methyl-1 -propanol in 125 ml of methylene chloride is added dropwise to a solution of 25.0 g of 2-thiophenecarboxyl chloride in 125 ml of methylene chloride while maintaining the temperature below 20° C. The mixture is stirred at room temperature for 2 hours and washed with water. The organic layer is dried over $MgSO_4$ and evaporated in vacuo to a residue. The residue is suspended in methylene chloride and 67.7 g of thionyl chloride added dropwise while maintaining the temperature below 30° C. The reaction mixture is stirred at room temperature for 18 hours and the volatiles evaporated in vacuo to a residue which is dissolved in water. The aqueous solution is rendered alkaline with 1N NaOH and extracted with ether. The organic layer is dried with $MgSO_4$ and concentrated in vacuo to give 31.1 g of the desired product as a yellowish oil.

Reference Example 51

4,5-Dihydro-4,4-dimethyl-2-[3-tributylstannyl)-2-thienyl]-oxazole

To a solution of 5.0 g of 4,5-dihydro-4,4 -dimethyl-2-(2-thienyl)-oxazole in 20 ml of ether is added dropwise 18.75 ml of butyl lithium while maintaining the temperature at −70° C. with stirring under nitrogen. The reaction mixture is stirred at −70° C. for 15 minutes and 30 minutes at 0° C. The reaction mixture is cooled to −70° C. and 10.0 g of tributyl tin chloride added. The reaction mixture is quenched with water and extracted with ether. The organic layer is washed with water (2×100 ml), dried and evaporated in vacuo to give 17.4 g of residue which is purified by chromatography on silica gel by elution with 7:1 hexane:ethyl acetate to give 12.4 g of a yellowish oil. MS(M+H=472) the next step is example 19

Reference Example 52

4-(4-Methylphenoxy)benzoic Acid

To a solution of 4.36 g of 4-methyl-phenol in 70 ml of dry dimethylsulfoxide under nitrogen with stirring is added 9.0 g of potassium t-butoxide. After stirring for 15 minutes, 0.1 g of copper metal is added followed by 10.0 g of 4-iodo-benzoic acid. The reactants are stirred under nitrogen while heating at 210° C. for 18 hours. The cooled reaction mixture is extracted with chloroform (2×900 ml) and the remaining water acidified with 2N HCl (pH=3) with ice bath cooling, to give 8.1 g of the desired product. MS(M+H=229.0)

Reference Example 53

4-(4-Methylphenoxy)benzoyl Chloride

A solution of 2.0 g of 4-(4-methylphenoxy)benzoic acid in 30 ml of methylene chloride is added 1.67 g of oxalyl chloride and the mixture refluxed for 30 minutes with stirring under nitrogen. The reaction mixture is evaporated in vacuo to a residue which is evaporated with carbon tetrachloride(2×30 ml).

Reference Example 54

4-[4-Propylphenyl]benzoyl Chloride

A mixture of 2.0 g of 4-(4-propylphenyl]benzoic acid and 30 ml of thionyl chloride is stirred at reflux for 45 minutes. The reaction mixture is evaporated in vacuo to a residue which is evaporated from carbon tetrachloride (2×50 ml) to give a residue which is dissolved in methylene chloride.

Reference Example 55

6-Hydroxynicotinic Acid Methyl Ester

To 500 ml of methyl alcohol, cooled to 0°–5° C. is added HCl gas over 30 minutes. The solution is allowed to reach room temperature and 50 g of 6 -hydroxynicotinic acid added. The reaction mixture is stirred at reflux for 2 days. The methyl alcohol is removed in vacuo and the residue suspended in 200 ml of water and poured into 300 ml of saturated aqueous $NaHCO_3$. The insoluble crystals are collected by filtration, washed with 500 ml of water and dried under vacuum at 60° C. to give 53.9 g of the desired product

Reference Example 56

Methyl 6-hydroxypyridine-3-carboxylate, o-triflate

A stirred solution of 8.0 g of pyridine and 5.0 g of 6-hydroxynicotinic acid methyl ester in 50 ml of methylene chloride is cooled to 0° C. under nitrogen while 22.0 g of trifluoromethanesulfonic anhydride is added. The reaction mixture is refluxed for 16 hours, evaporated in vacuo to a residue which is stirred with 200 ml of ice water and the solid collected. The solid is dried in a vacuum oven at 30° C. to give 7.0 g of the desired product.

Reference Example 57

2-(Tributylstannyl)thiophene

A solution of 8.4 g of thiophene in 200 ml of ether is stirred, cooled to 0° C. under nitrogen while 48.0 g of butyl lithium is added dropwise via syringe. After stirring for 1 hour, the reaction mixture is cooled to −78° C. and 35.0 ml of tributyl tin chloride is added dropwise via syringe. Following stirring at room temperature for 30 minutes, the reaction mixture is quenched with 60 ml of water, poured over crushed ice and extracted with ether (3×200 ml). The organic layer is dried and evaporated in vacuo to give 46.2 g of the desired product as a residue.

Reference Example 58

Methyl 6-(2-thienyl)pyridine-3-carboxylate

A solution of 2.0 g of (methyl 6-hydroxypyridine-3 -carboxylate, o-triflate) and 5.23 g of 2-(tributylstannyl)thiophene in 50 ml of dry toluene is stirred under nitrogen at reflux for 16 hours in the presence of tetrakis(triphenylphosphine)palladium(O). The reaction mixture is diluted with 50 ml of chloroform and filtered through a pad of diatomaceous earth. The filtrate is evaporated in vacuo to a residue which is extracted and decanted (2×100 ml) with 1:1 ether:petroleum ether. The combined extracts are evaporated in vacuo to give 1.6 g of the desired product as a residue.

Reference Example 59

6-(2-Thienyl)pyridine-3-carboxylic acid

A solution of 2.0 g of methyl 6-(2 -thienyl)pyridine-3-carboxylate in 100 ml of methyl alcohol and 50 ml of 5N sodium hydroxide is stirred at room temperature for 16 hours under nitrogen. The reaction mixture is evaporated in vacuo to about one quarter of the volume and then diluted with 150 ml of cold water. The pH is adjusted to 4 with acetic acid and the desired white product collected, washed with 400 ml of cold water until neutral. The solid is washed with 50 ml of petroleum ether and dried under vacuum to 40° C. to give the desired product.

Reference. Example 60

6-(2-Thienyl)pyridine-3-carbonyl chloride

A mixture of 1.8 g of 6-(2-thienyl)pyridine-3 -carboxylic acid in 50 ml of thionyl chloride is refluxed under dry conditions for 1 hour. The reaction mixture is evaporated to dryness and evaporated again from 50 ml of carbon tetrachloride to a residue. The residue is dissolved in 60 ml of methylene chloride and used further reactions.

Example 1

10,11-Dihydro-10-[4-(2-thienyl)benzoyl]-5H-pyrrolo[2,1-c][1,4]benzodiazepine A mixture of 1.64 g of 10,11-dihydro-10-(4 -iodobenzoyl)-5H-pyrrolo[2,1-c][1,4]benzodiazepine, 1.9 g of 2-tri-n-butylstannyl thiophene and 200 mg of tetrakis(triphenylphosphine)palladium(O) in 200 ml of toluene is refluxed under nitrogen for 16 hours. The reaction mixture is evaporated in vacuo to a residue which is purified by column chromatography on silica gel by elution with 5:1 hexane:ethyl acetate to give 1.2 g of the desired product as a solid. Mass spectrum: M+H:371.

Example 2

10,11-Dihydro-10-[4-(2-nitrophenyl)benzoyl]-5H-pyrrolo[2,1-c][1,4]benzodiazepine A mixture of 3.0 g of 10,11-dihydro-10-[4 -(tributylstannyl)benzoyl]-5H-pyrrolo[2,1-c][1,4]benzodiazepine, 200 mg of tetrakis(triphenylphosphine)palladium(O) and 2.0 g of 1-bromo-2-nitrobenzene in 200 ml of toluene is refluxed for 16 hours. The reaction mixture is filtered and the filtrate evaporated in vacuo to a residue which is purified by column chromatography on silica gel by elution with 30% ethyl acetate-hexane to give 1.2 g of the desired product as a solid. Mass spectrum: M+H:410.

Example 3

10,11-Dihydro-10-[4-(3,5-difluorophenyl)benzoyl]-5H-pyrrolo[2,1-c][1,4]benzodiazepine A mixture of 1.5 g of 10,11-dihydro-10-[4 -(tributylstannyl)benzoyl]-5H-pyrrolo[2,1-c][1,4]benzodiazepine, 1 ml of 3,5-difluoro-1-bromobenzene and 200 mg of tetrakis(triphenylphosphine)palladium(O) in 200 ml of toluene is refluxed for 16 hours. The reaction mixture is filtered and the filtrate evaporated in vacuo to a residue which is purified by column chromatography on silica gel by elution with 30% ethyl acetate-hexane to give 700 mg of the desired product as a solid. Mass spectrum: M+H:401.

Example 4

10,11-Dihydro-10-[4-(phenylethynyl)-5H-pyrrolo[2,1-c]1,4]benzodiazepine

A mixture of 2.0 g of 10,11-dihydro-10-[4 -iodobenzoyl)-5H-pyrrolo[2,1-c][1,4]benzodiazepine, 1.0 g of phenylacetylene and 200 mg of Pd(II) chloride is refluxed in 250 ml of acetonitrile for 4 hours. The reaction mixture is cooled to room temperature and the resulting yellow crystalline solid collected, dried and crystallized from methyl alcohol to afford 1.2 g of the desired product. Mass spectrum: M+H:389.

Example 5

10,11-Dihydro-10-[4-(2-methylphenyl)benzoyl]-5H-pyrrolo[2,1-c][1,4]benzodiazepine A mixture of 2.0 g of 10,11-dihydro-10-(4 -iodobenzoyl)-5H-pyrrolo[2,1-c][1,4]benzodiazepine, 3.0 g of 2-(tributylstannyl)toluene and 200 mg of tetrakis(triphenylphosphine- )palladium(O) in 200 ml of toluene is refluxed for 16 hours. The reaction mixture is evaporated in vacuo to a residue which is purified by column chromatography on silica gel by elution with 30% ethyl acetate-hexane to give 1.0 g of the desired product as a solid. Mass spectrum: M+H:379.

Example 6

10,11-Dihydro-3-[(dimethylamino)methyl]-10-[4-(2 -thienyl)benzoyl]-5H-pyrrolo[2,1-c][1,4]benzodiazepine A mixture of 400 mg of 10,11-dihydro-10-[4-(2 -thienyl) benzoyl]-5H-pyrrolo[2,1-c][1,4]benzodiazepine, 10 ml of 40% formalin and 10 ml of 40% N,N-dimethylamine in 50 ml of 1:1 tetrahydrofuran:methyl alcohol is refluxed for 3 hours. The reaction mixture is evaporated in vacuo to a residue which is extracted with chloroform, washed with water, dried over $Na_2SO_4$, filtered and the filtrate evaporated in vacuo to give a residue which is purified by column chromatography on silica gel by elution with 30% ethyl acetate-hexane to give 300 mg of the desired product as a solid. Mass spectrum: M+H:428.

Example 7

5-([1,1'-Biphenyl]-4-ylcarbonyl)-5,10-dihydro-4 H-pyrazolo[5,1-c][1,4]benzodiazepine To a stirred solution of 185 mg of 5,10 -dihydro-4H-pyrazolo[5,1-c][1,4]benzodiazepine in 50 ml of methylene chloride containing 2.0 ml of triethylamine is slowly added a solution of 300 mg of 4-biphenylcarbonyl chloride in 10 ml of methylene chloride at room temperature. The reaction mixture is stirred at room temperature for 16 hours and evaporated in vacuo to give a residue. The residue is extracted with chloroform, washed with water, dried over $Na_2SO_4$, filtered and the filtrate evaporated in vacuo to give a residue which is purified by column chromatography on silica gel by elution with 30% ethyl acetate-hexane to give 250 mg of the desired product as a solid. Mass spectrum: M+H:366.

Example 8

10,11-Dihydro-10-[[2'-(trifluoromethyl)[1,1'-biphenyl]-4-yl]carbonyl-5H-pyrrolo[2,1-c][1,4]benzodiazepine To a solution of 2.0 g of 10,11-dihydro-10-(4 -iodobenzoyl)-5H-pyrrolo[2,1-c][1,4]benzodiazepine and 4.2 g of m-trifluoromethyltributyltin in 100 ml of toluene and 30 ml of N,N-dimethylformamide under nitrogen is added 0.5 g of tetrakis(triphenylphosphine)palladium and the mixture is heated to 120° C. for 12 hours. The toluene is evaporated in vacuo and the oily residue diluted with 50 ml of chloroform and filtered through diatomaceous earth. The filtrate is washed with water (3×50 ml), dried ($Na_2SO_4$) and evaporated in vacuo to give a residue which is columned on silica gel by elution with 7:1 to 1:1 ethyl acetate:hexane to give 1.75 g of the desired product as a solid, m.p. 138°–141° C.; M+H=433.4; M+Na=455.4.

Example 9

10,11-Dihydro-10-[4-(2-pyridinyl)benzoyl]-5 H-pyrrolo[2,1-c][1,4]benzodiazepine

To a solution of 2.0 g of 10,11-dihydro-10-(4 -iodobenzoyl)-5H-pyrrolo[2,1-c][1,4]benzodiazepine and 4.39 g of 2-[(tri-n-butyl)stannyl]pyridine in 30 ml of toluene under nitrogen is added 0.2 g of tetrakis(triphenylphosphine)palladium and the mixture heated to 120° C. for 16 hours. The toluene is evaporated in vacuo and the oily residue diluted with 50 ml of chloroform and washed with water, dried ($Na_2SO_4$), filtered through diatomaceous earth and evaporated in vacuo to give a residue which is columned on silica gel by elution with 7:1 to 1:1 ethyl acetate:hexane to give 1.44 g of the desired product as a solid, m.p. 170°–172° C.; M+H=366.1; M+Na=388.1.

Example 10

10,11-Dihydro-10-[4-(2-thiazolyl)benzoyl]-5 H-pyrrolo[2,1-c][1,4]benzodiazepine

To a solution of 1.1 g of 10,11-dihydro-10-(4 -iodobenzoyl)-5H-pyrrolo[2,1-c][1,4]benzodiazepine and 1.49 g of 2-(tributylstannyl)thiazole (Reference Example 48) in 50 ml of toluene under nitrogen is added 0.2 g of tetrakis(triphenylphosphine)palladium and the mixture heated to 120° C. for 16 hours. The toluene is evaporated in vacuo to a residue which is columned on silica gel by elution with 7:1 to 1:1 ethyl acetate:hexane to give 0.62 g of the desired product as an amphorous solid; M+H=372.3; M+Na=395.3.

Example 11

10,11-Dihydro-10-[4-[(4-methylphenyl)thio]benzoyl-5 H-pyrrolo[2,1-c][1,4]benzodiazepine To a solution of 1.0 g of 10,11-dihydro-5 H-pyrrolo[2,1-c][1,4]benzodiazepine in 50 ml of dry methylene chloride, under nitrogen, and cooled to 0° C. is added dropwise a solution of 2.50 g of 4-[(4-methylphenyl)thio]benzoyl chloride in 30 ml of methylene chloride. A 5.0 ml portion of tri-ethylamine is added and the reaction mixture stirred at room temperature for 16 hours. The reaction mixture is diluted with 50 ml of chloroform and washed with 50 ml each of water, 2N HCl, water, saturated $NaHCO_3$ and water. The organic layer is dried ($Na_2SO_4$) and columned on silica gel by elution with 7:1 to 3:1 ethyl acetate:hexane to give 1.96 g of the desired product as a solid. M+H 411.2 M+Na 433.2.

Example 12

10,11-Dihydro-10-[4-Phenylsulfonyl]benzoyl]-5 H-pyrrolo[2,1-c][1,4]benzodiazepine To a solution of 1.0 g of 10,11-dihydro-5 H-pyrrolo[2,1-c][1,4]benzodiazepine in 30 ml of dry methylene chloride, under nitrogen, and cooled to 0° C. is added dropwise a solution of 1.82 g of 4-(phenylsulfonyl)benzoyl chloride in 30 ml of methylene chloride. A 7.0 ml portion of tri-ethylamine is added and the reaction mixture stirred at room temperature for 16 hours. The reaction mixture is diluted with 50 ml of chloroform and washed with 50 ml each of water, 2N HCl, water, saturated $NaHCO_3$ and water. The organic layer is dried ($Na_2SO_4$) and columned on silica gel by elution with 7:1 to 3:1 ethyl acetate:hexane to give 2.2 g of the desired product as a solid. M+H 429.2 M+Na 451.2.

Example 13

10,11-Dihydro-10-[4-[(4-methylphenyl)sulfonyl]benzoyl]-5H-pyrrolo[2,1-c][1,4]benzodiazepine A mixture of 2.13 g of 4-[(4-methylphenyl)sulfonyl]benzoyl chloride (Reference Example 42) and 1.0 g of 10,11-dihydro-5H-pyrrolo[2,1-c][1,4]benzodiazepine in 30 ml of methylene chloride containing 7 ml of triethylamine is stirred under nitrogen atmosphere for 16 hours. The reaction mixture is diluted with ? ml of chloroform and washed with 2N HCl, water, saturated NaHCO$_3$ and water. The organic layer is dried (Na$_2$SO$_4$) and columned on silica gel by elution with 7:1 to 3:1 ethyl acetate:hexane to give 1.3 g of the desired product as a solid. M+H 443.2; M+Na 465.2.

Example 14

10,11-Dihydro-10-[[4'-(2-propenyloxy)[1,1'-biphenyl]-4-yl]carbonyl]-5H-pyrrolo[2,1-c][1,4]benzodiazepine To a solution of 3.3 g of 10,11-dihydro-5 H-pyrrolo[2,1-c][1,4]benzodiazepine in 60 ml of dry methylene chloride, under nitrogen, and cooled to 0° C. is added 22.0 ml of triethylamine followed by a solution of 1.2 equivalents of 4'-(2-propenyloxy)-[1,1'-biphenyl]-4-carbonyl chloride in 20 ml of methylene chloride. The reaction mixture is stirred at room temperature for 16 hours. The reaction mixture is diluted with 50 ml of chloroform and washed with 50 ml each of water, 2N HCl, water, saturated NaHCO$_3$ and water. The organic layer is dried (Na$_2$SO$_4$) and columned on silica gel by elution with 7:1 to 3:1 ethyl acetate:hexane to give 4.8 g of the desired product as a solid. M+H 421.2 M+Na 443.2.

Example 15

10,11-Dihydro-10-[4-(phenylthio)benzoyl]-5H-pyrrolo[2,1 -c][1,4]benzodiazepine

To a solution of 1.0 g of 10,11-dihydro-5 H-pyrrolo[2,1-c][1,4]benzodiazepine in 50 ml of dry methylene chloride, under nitrogen, and cooled to 0° C. is added 5.0 ml of triethylamine followed by a solution of 2.16 g of 4-(phenylthio)benzoyl chloride (Reference Example 34) in 30 ml of methylene chloride. The reaction mixture is stirred at room temperature for 16 hours. The reaction mixture is diluted with 50 ml of chloroform and washed with 50 ml each of water, 2N HCl, water, saturated NaHCO$_3$ and water. The organic layer is dried (Na$_2$SO$_4$) and columned on silica gel by elution with 7:1 to 3:1 ethyl acetate:hexane to give 1.92 g of the desired product as a solid. M+H 397.1 M+Na 419.1.

Example 16

10-(4-Benzoylbenzoyl)-10,11-dihydro-5H-pyrrolo[2,1-c][1,4]benzodiazepine

A mixture of 2.16 g of 4-(benzoyl)benzoyl chloride (Reference Example 36) and 1.0 g of 10,11 -dihydro-5H-pyrrolo[2,1-c][1,4]benzodiazepine in 30 ml of methylene chloride containing 7 ml of triethylamine is stirred under nitrogen atmosphere for 16 hours. The reaction mixture is diluted with 50 ml of chloroform and washed with 2N HCl, water, saturated NaHCO$_3$ and water. The organic layer is dried (Na$_2$SO$_4$) and columned on silica gel by elution with 7:1 to 3:1 ethyl acetate:hexane to give 1.8 g of the desired product as a solid. M+H 393.2; M+Na 415.2.

Example 17

5-([1,1'-Biphenyl]-4-ylcarbonyl)-4,5-dihydropyrrolo[1,2-a]quinoxaline

To a mixture of 0.5 g of 4,5-dihydropyrrolo[1,2-a]quinoxaline and 0.96 g of 4-biphenylcarbonyl chloride in 50 ml of methylene chloride under argon is added 7.0 ml of triethylamine followed by stirring at room temperature for 16 hours. The reaction mixture is diluted with 50 ml of chloroform and washed with water, 2N HCl, saturated NaHCO$_3$ and water. The organic layer is dried (Na$_2$SO$_4$) and columned on silica gel by elution with 7:1 to 1:1 ethyl acetate:hexane to give 0.87 g of the desired product as a solid. M+H 351.2; M+Na 373.2.

Example 18

10,11-Dihydro-10-[4-(4-methylphenoxy)benzoyl]-5 H-pyrrolo[2,1-c][1,4]benzodiazepine To a stirred solution of 1.0 g of 10,11 -dihydro-5H-pyrazolo[5,1-c][1,4]benzodiazepine in 30 ml of methylene chloride, under nitrogen, while cooling to 0° C. is added dropwise 30 ml of triethylamine followed by a solution of 1.2 equivalents of 4-(4-methylphenoxy)benzoyl chloride in 10 ml of CH$_2$Cl$_2$ (Reference Example 53) prepared from Reference Example 52 and thionyl chloride. The reactants are stirred at room temperature for 16 hours and concentrated in vacuo to a residue. The residue is dissolved in methylene chloride, washed with water, 2N HCl, water, saturated aqueous NaHCO$_3$, water and dried (MgSO$_4$) and evaporated in vacuo to give 2.2 g of the desired product. MS(M+H=395.1)

Example 19

10-([1,1'-Biphenyl]-4-ylcarbonyl)-10,11-dihydro-5 H-pyrrolo[2,1-c][1,4]benzodiazepine A solution of 0.9 g of 10,11-dihydro-5 H-pyrazolo[2,1-c][1,4]benzodiazepine in 30 ml of methylene chloride is cooled to 0° C. and 1.6 ml of triethylamine added. A solution of 1.2 equivalents of 4-biphenylcarbonyl chloride in 10 ml of CH$_2$Cl$_2$ is added and the reaction mixture stirred at room temperature for 16 hours. The reaction mixture is diluted with 50 ml of chloroform and washed with 20 ml each of water, 2N HCl, water, saturated aqueous NaHCO$_3$ and water. The organic layer is dried and evaporated in vacuo to a residue. The residue is purified by column chromatography on silica gel by elution with 3:1 hexane:ethyl acetate to give 1.5 g of the desired product.

Example 20

10-([1,1'-Biphenyl]-4-ylcarbonyl)-10,11-dihydro-N,N-dimethyl- 5H-pyrrolo[2,1-c][1,4]benzodiazepine-3-methanamine A solution of 0.6 g of 10-([1,1'-Biphenyl]-4 -ylcarbonyl)-10,11-dihydro-5H-pyrrolo[2,1-c][1,4] benzodiazepine in 50 ml of 1:1 methyl alcohol:tetrahydrofuran is stirred under nitrogen while 10 ml of a 30% solution of formaldehyde, 10 ml of a 40% solution of dimethylamine and 2 drops of acetic acid is added. The reaction mixture is stirred at room temperature for 16 hours then extracted with chloroform (3×100 ml) and the organic layer washed with saturated aqueous NaHCO$_3$ (2×50 ml), water (2×50 ml), dried and evaporated in vacuo to give 0.68 g of a residue which is stirred with petroleum ether to give 0.62 g of the desired product as a crystalline solid, m.p. 85°–87° C.

Example 21

10,11-Dihydro-10-[(4'-propyl[1,1'-biphenyl]-4-yl)carbonyl]-5H-pyrrolo[2,1-c][1,4]benzodiazepine To a stirred solution of 2.0 g of 10,11 -dihydro-5H-pyrrolo[2,1-c][1,4]benzodiazepine in 30 ml of methylene chloride, under nitrogen, while cooling to 0° C. is added dropwise 30 ml of triethylamine followed by a solution of 4'-(propyl)[1,1'-biphenyl]-4-carbonyl chloride in 10 ml of methylene dichloride. The reactants are stirred at room temperature for 16 hours. The reaction mixture is poured in ice water and extracted with methylene chloride (3×50 ml) The organic layer is, washed with water, 2N citric acid, saturated aqueous NaHCO$_3$, water and dried (MgSO$_4$) and evaporated in vacuo to give a residue which is purified by column chromatography on silica gel with ethyl acetate-hexane to give 1.4 g of the desired product as a crystalline solid, m.p. 118°–120° C. MS(M+H=407.3; M+Na=429.3)

Example 22

10,11-Dihydro-10-[2-(2-thienyl)pyridin-5-yl)carbonyl]-5H-pyrrolo[2,1-c][1,4]benzodiazepine A solution of 5 mmol of 10,11-dihydro-5 H-pyrazolo[2,1-c][1,4]benzodiazepine in 30 ml of methylene chloride is cooled to 0° C. and 10.0 ml of triethylamine added. A solution of 6 mmol of Reference Example 60 is added and the reaction mixture stirred at room temperature for 16 hours. The reaction mixture is diluted with 60 ml of chloroform and washed with 40 ml each of water, saturated aqueous NaHCO$_3$ and water. The organic layer is dried and evaporated in vacuo to a residue. The residue is purified by column chromatography on silica gel by elution with 3:1 hexane:ethyl acetate to give the desired product.

UTILITY TESTING

Binding Assay to Rat Hepatic V1 Receptors

Rat liver plasma membranes expressing the vasopressin V$_1$ receptor subtypes are isolated by sucrose density gradient according to the method described by Lesko et al., (1973). These membranes are quickly suspended in 50.0 mM Tris.HCl buffer, pH 7.4, containing 0.2% bovine serum albumin (BSA) and 0.1 mM phenylmethylsulfonylfluoride (PMSF) and kept frozen at −70° C. until used in subsequent binding experiments. For binding experiments, the following is added to the wells of a ninety-six well format microtiter plate: 100 μl of 100.0 mM Tris.HCl buffer containing 10.0 mM MgCl$_2$, 0.2% heat inactivated BSA and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 μl of [phenylalanyl- 3,4,5,-$^3$H] vasopressin (S.A. 45.1 Ci/mmole) at 0.8 nM, and the reaction initiated by the addition of 80 μl of tissue membranes containing 20 μg of tissue protein. The plates are kept undisturbed on the bench top at room temperature for 120 min. to reach equilibrium. Non-specific samples are assayed in the presence of 0.1 μM of the unlabeled antagonist phenylalanylvasopressin, added in 20.0 μl volume.

For test compounds, these are solubilized in 50% dimethylsulfoxide (DMSO) and added in 20.0 μl volume to a final incubation volume of 200 μl. Upon completion of binding, the content of each well is filtered off, using a Brandel®, cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for IC$_{50}$ values by the LUNDON-2 program for competition (LUNDON SOFTWARE, Ohio). Binding Assay to Rat Kidney Medullary V$_2$ Receptors Medullary tissues from rat kidneys are dissected out, cut into small pieces and soaked in a 0.154 mM sodium chloride solution containing 1.0 mM EDTA with many changes of the liquid phase, until the solution is clear of blood. The tissue is homogenized in a 0.25M sucrose solution containing 1.0 mM EDTA and 0.1 mM PMSF using a Potter-Elvehjem homogenizer with a teflon pestle. The homogenate is filtered through several layers (4 layers) of cheese cloth. The filtrate is rehomogenized using a dounce homogenizer, with a tight fitting pestle. The final homogenate is centrifuged at 1500× g for 15 min. The nuclear pellet is discarded and the supernatant fluid recentrifuged at 40,000× g for 30 min. The resulting pellet formed contains a dark inner part with the exterior, slightly pink. The pink outer part is suspended in a small amount of 50.0 mM Tris.HCl buffer, pH 7.4. The protein content is determined by the Lowry's method (Lowry et al., J. Biol. Chem., 1953). The membrane suspension is stored at −70° C., in 50.0 mM Tris.HCl, containing 0.2% inactivated BSA and 0.1 mM PMSF in aliquots of 1.0 ml containing 10.0 mg protein per ml of suspension until use in subsequent binding experiments.

For binding experiments, the following is added in μl volume to wells of a 96 well format of a microtiter plate: 100.0 μl of 100.0 mM Tris.HCl buffer containing 0.2% heat inactivated BSA, 10.0 mM MgCl$_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 μl of [$^3$H] Arginine$^8$, vasopressin (S.A. 75.0 Ci/mmole) at 0.8 nM and the reaction initiated by the addition of 80.0 μl of tissue membranes (200.0 μg tissue protein). The plates are left undisturbed on the bench top for 120 min to reach equilibrium. Non-specific binding is assessed in the presence of 1.0 μM of unlabeled ligand, added in 20 μl volume. For test compounds, these are solubilized in 50% dimethylsulfoxide (DMSO) and added in 20.0 μl volume to a final incubation volume of 200 μl. Upon completion of binding, the content of each well is filtered off, using a Brandel, cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for IC$_{50}$ values by the LUNDON-2 program for competition (LUNDON SOFTWARE, Ohio). The results of this test on representative compounds of this invention are shown in Table I.

Radioligand Binding Experiments with Human Platelet Membranes (a) Platelet Membrane Preparation Frozen platelet rich plasma (PRP), (Platelet Source: Hudson Valley Blood Services, Westchester Medical Center, Valhalla, N.Y.) are thawed to room temperature. The tubes containing the PRP are centrifuged at 16,000× g for 10 min. at 4° C. and the supernatant fluid discarded. The platelets resuspended in an equal volume of 50.0 mM Tris.HCl, pH 7.5 containing 120 mM NaCl and 20.0 mM EDTA. The suspension is recentrifuged at 16,000× g for 10 min. This washing step is repeated one more time. The wash discarded and the lysed pellets homogenized in low ionic strength buffer of Tris.HCl, 5.0 mM, pH 7.5 containing 5.0 mM EDTA. The homogenate is centrifuged at 39,000× g for 10 min. The resulting pellet is resuspended in Tris.HCl buffer, 70.0 mM, pH 7.5 and recentrifuged at 39,000× g for 10 min. The final pellet is resuspended in 50.0 mM Tris.HCl buffer pH 7.4 containing 120 mM NaCl and 5.0 mM KCl to give 1.0–2.0 mg protein per ml of suspension.

(b) Binding to Vasopressin V1 receptor subtype in Human Platelet Membranes

In wells of a 96 well format microtiter plate, add 100 μl of 50.0 mM Tris.HCl buffer containing 0.2% BSA and a mixture of protease inhibitors (aprotinin, leupeptin etc.). Then add 20 μl of [$^3$H]Ligand (Manning or Arg$^8$Vasopressin), to give final concentrations ranging from 0.01 to 10.0 nM. Initiate the binding by adding 80.0 μl of platelet suspension (approx. 100 μg protein). Mix all reagents by pipetting the mixture up and down a few times. Non specific binding is measured in the presence of 1.0 lM of unlabeled ligand (Manning or Arg$^8$Vasopressin). Let the mixture stand undisturbed at room temperature for ninety (90) min. Upon this time, rapidly filter off the incubate under vacuum suction over GF/B filters, using a Brandel Harvester. Determine the radioactivity caught on the filter disks by the addition of liquid scintillant and counting in a liquid scintillator.

Binding to Membranes of Mouse Fibroblast Cell Line (LV-2) Transfected with the cDNA Expressing the Human V2 Vasopressin Receptor (a) Membrane Preparation Flasks of 175 ml capacity, containing attached cells grown to confluence, are cleared of culture medium by aspiration. The flasks containing the attached cells are rinsed with 2×5 ml of phosphate buffered saline (PBS) and the liquid aspirated off each time. Finally, 5 ml of an enzyme free dissociation Hank's based solution (Specialty Media, Inc., Lafayette, N.J.) is added and the flasks are left undisturbed for 2 min. The content of all flasks is poured into a centrifuge tube and the cells pelleted at 300× g for 15 min. The Hank's based solution is aspirated off and the cells homogenized with a polytron at setting #6 for 10 sec in 10.0 mM Tris.HCl buffer, pH 7.4 containing 0.25M sucrose and 1.0 mM EDTA. The homogenate is centrifuged at 1500× g for 10 min to remove ghost membranes. The supernatant fluid is centrifuged at 100,000× g for 60 min to pellet the receptor protein. Upon completion, the pellet is resuspended in a small volume of 50.0 mM Tris.HCl buffer, pH 7.4. The protein content is determined by the Lowry method and the receptor membranes are suspended in 50.0 mM Tris.HCl buffer containing 0.1 mM phenylmethylsulfonylfluoride (PMSF) and 0.2% bovine serum albumin (BSA) to give 2.5 mg receptor protein per ml of suspension.

(b) Receptor Binding

For binding experiments, the following is added in μl volume to wells of a 96 well format of a microtiter plate: 100.0 μl of 100.0 mM Tris.HCl buffer containing 0.2% heat inactivated BSA, 10.0 mM MgCl$_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF., 20.0 μl of [$^3$H] Arginine$^8$, vasopressin (S.A. 75.0 Ci/mmole) at 0.8 nM and the reaction initiated by the addition of 80.0 μl of tissue membranes (200.0 μg tissue protein). The plates are left undisturbed on the bench top for 120 min to reach equilibrium. Non specific binding is assessed in the presence of 1.0 μM of unlabeled ligand, added in 20 μl volume. For test compounds, these are solubilized in 50% dimethylsulfoxide (DMSO) and added in 20.0 μl volume to a final incubation volume of 200 μl. Upon completion of binding, the content of each well is filtered off, using a Brandel, cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for IC$_{50}$ values by the LUNDON-2 program for competition (LUNDON SOFTWARE, Ohio).

TABLE I

Binding Assay to Rat Hepatic V$_1$ Receptors and Rat Kidney Medullary V$_2$ Receptors of *Binding to V$_1$ Receptor Subtype in Human Platelet and **Binding to Membranes of Mouse Fibroblast Cell Line(LV-2) Transfected with the cDNA Expressing the Human V$_2$ Receptor

| Ex. No. | Structure | V$_1$ IC$_{50}$ (μM) | V$_2$ IC$_{50}$ (μM) |
|---|---|---|---|
| 1 | (structure) | 0.013* | 0.51** |

TABLE I-continued

Binding Assay to Rat Hepatic $V_1$ Receptors and Rat Kidney Medullary $V_2$ Receptors of *Binding to $V_1$ Receptor Subtype in Human Platelet and **Binding to Membranes of Mouse Fibroblast Cell Line(LV-2) Transfected with the cDNA Expressing the Human $V_2$ Receptor

| Ex. No. | Structure | $V_1$ $IC_{50}$ (μM) | $V_2$ $IC_{50}$ (μM) |
|---|---|---|---|
| 2 | 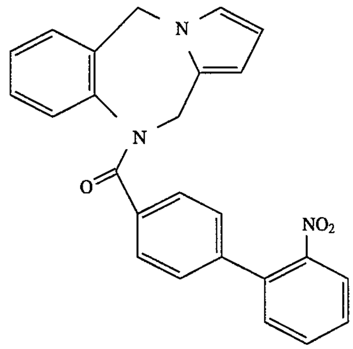 | 0.064* | 0.096** |
| 3 | 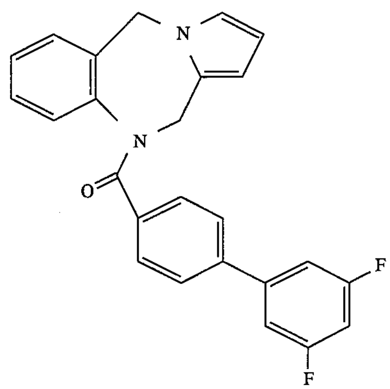 | 0.085* | 2.5** |
| 4 | 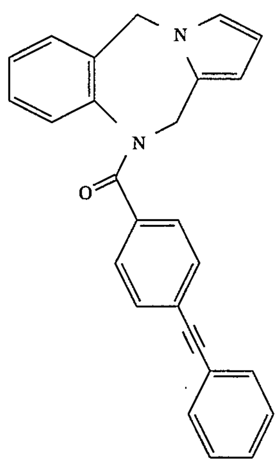 | 1 μM (35%)* | 1 μM (63%)** |

TABLE I-continued
Binding Assay to Rat Hepatic $V_1$ Receptors and Rat Kidney Medullary $V_2$ Receptors of *Binding to $V_1$ Receptor Subtype in Human Platelet and **Binding to Membranes of Mouse Fibroblast Cell Line(LV-2) Transfected with the cDNA Expressing the Human $V_2$ Receptor
| Ex. No. | Structure | $V_1$ IC$_{50}$ (μM) | $V_2$ IC$_{50}$ (μM) |
|---|---|---|---|
| 5 | 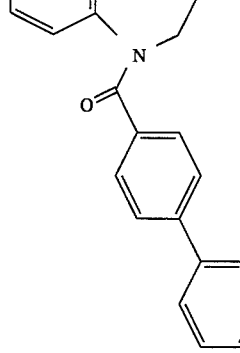 | 0.088* | 2.0** |
| 6 | 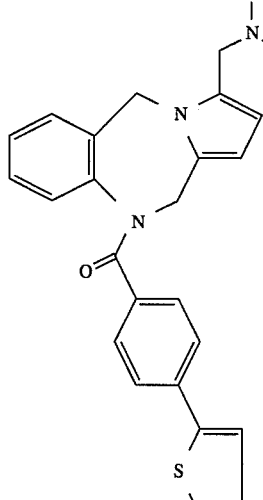 | 0.063* | 15 μM** |
| 7 | 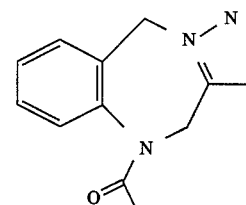 | 0.014* | 1.7** |

TABLE I-continued

Binding Assay to Rat Hepatic V₁ Receptors and Rat Kidney
Medullary V₂ Receptors of *Binding to V₁ Receptor
Subtype in Human Platelet and **Binding to Membranes of
Mouse Fibroblast Cell Line(LV-2) Transfected with the
cDNA Expressing the Human V₂ Receptor

| Ex. No. | Structure | $V_1$ $IC_{50}$ (μM) | $V_2$ $IC_{50}$ (μM) |
|---|---|---|---|
| 8 | 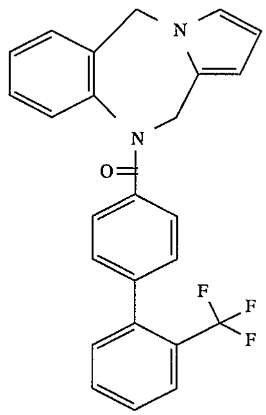 | 0.67 | 3.3 |
| 9 | 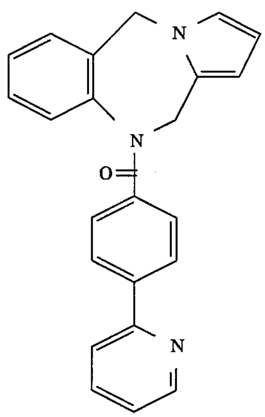 | 0.4 | 1.2 |
| 10 | 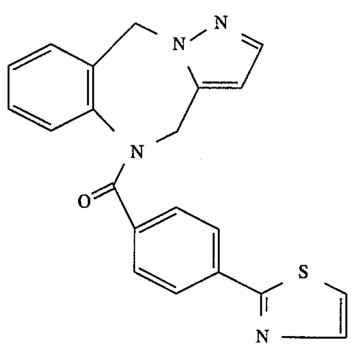 | 10 μM (58%) | 10 μM (48%) |

TABLE I-continued

Binding Assay to Rat Hepatic $V_1$ Receptors and Rat Kidney Medullary $V_2$ Receptors of *Binding to $V_1$ Receptor Subtype in Human Platelet and **Binding to Membranes of Mouse Fibroblast Cell Line(LV-2) Transfected with the cDNA Expressing the Human $V_2$ Receptor

| Ex. No. | Structure | $V_1$ IC$_{50}$ (µM) | $V_2$ IC$_{50}$ (µM) |
|---|---|---|---|
| 11 | 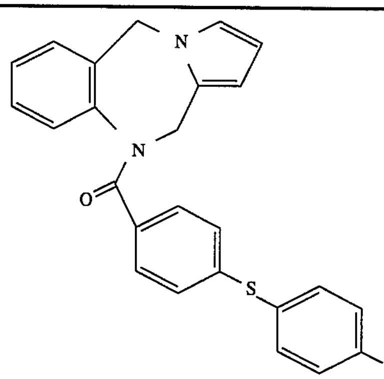 | 1 µM (15%)* | 1 µM (32*)** |
| 12 | 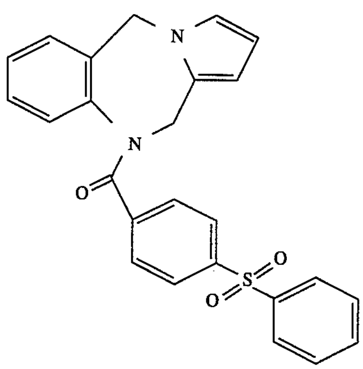 | 10 µM (42%) | 10 µM (66%) |
| 13 | 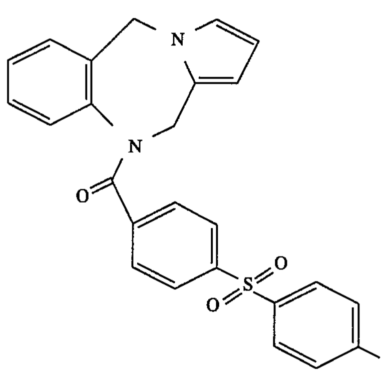 | 0.021* | 1 µM (51%) |

TABLE I-continued

Binding Assay to Rat Hepatic V₁ Receptors and Rat Kidney
Medullary V₂ Receptors of *Binding to V₁ Receptor
Subtype in Human Platelet and **Binding to Membranes of
Mouse Fibroblast Cell Line(LV-2) Transfected with the
cDNA Expressing the Human V₂ Receptor

| Ex. No. | Structure | $V_1$ IC$_{50}$ (μM) | $V_2$ IC$_{50}$ (μM) |
|---|---|---|---|
| 14 | 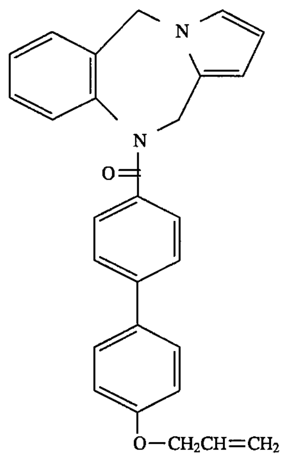 | 10 μM (9%)* | 1 μM (63%) |
| 15 | 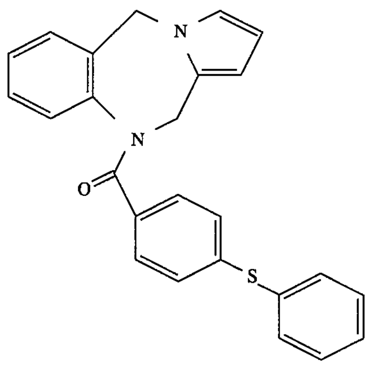 | 1 μM (47%)* | 1 μM (42%)** |
| 16 | 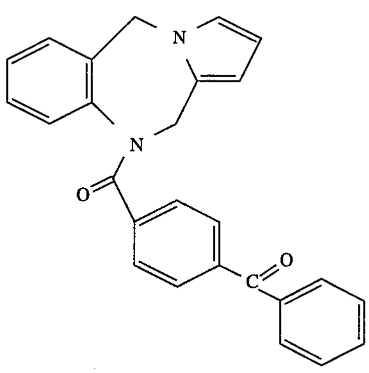 | 10 μM (82%)* | 1 μM (42%) |

TABLE I-continued

Binding Assay to Rat Hepatic $V_1$ Receptors and Rat Kidney Medullary $V_2$ Receptors of *Binding to $V_1$ Receptor Subtype in Human Platelet and **Binding to Membranes of Mouse Fibroblast Cell Line(LV-2) Transfected with the cDNA Expressing the Human $V_2$ Receptor

| Ex. No. | Structure | $V_1$ IC$_{50}$ (μM) | $V_2$ IC$_{50}$ (μM) |
|---|---|---|---|
| 17 | 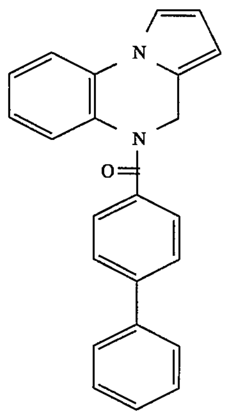 | 1 μM (63%) | 1 μM (55%) |
| 18 | 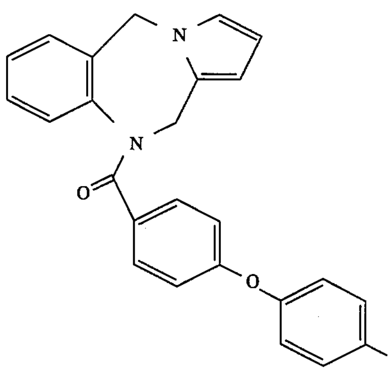 | 0.28* | 1 μM (50%)** <br> 1 μM (58%) |
| 19 | 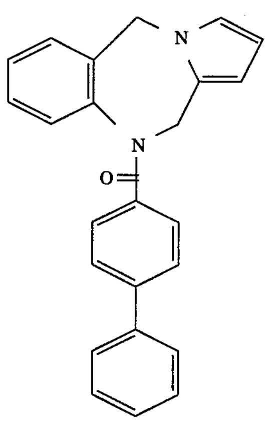 | 0.0029* | 0.39** |

TABLE I-continued

Binding Assay to Rat Hepatic $V_1$ Receptors and Rat Kidney
Medullary $V_2$ Receptors of *Binding to $V_1$ Receptor
Subtype in Human Platelet and **Binding to Membranes of
Mouse Fibroblast Cell Line(LV-2) Transfected with the
cDNA Expressing the Human $V_2$ Receptor

| Ex. No. | Structure | $V_1$ IC$_{50}$ (μM) | $V_2$ IC$_{50}$ (μM) |
|---|---|---|---|
| 20 | 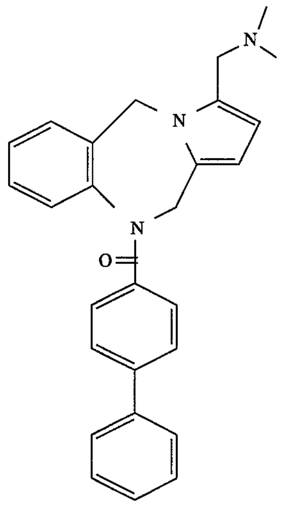 | 0.013* | 10 μM (78%)** |
| 21 | 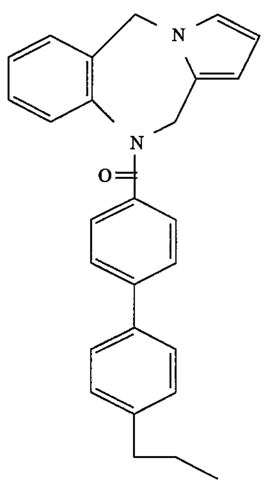 | 0.012* | 0.058** |
| 22 | 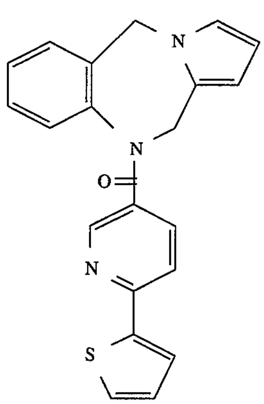 | 0.96* | 3.6** |

Vasopressin $V_2$ Antagonist Activity in Conscious Hydrated Rats

Conscious hydrated rats are treated with compounds under study from 0.1 to 100 mg/kg orally or vehicle. Two to four rats are used for each compound. One hour later, arginine vasopressin (AVP, antidiuretic hormone, ADH) dissolved in peanut oil is administered at 0.4 μg/kg intraperitoneally. Two rats in each test would not receive arginine vasopressin but only the vehicle (peanut oil) to serve as water-loading control. Twenty minutes later each rat is given 30 mL/kg of deionized water orally by gavage and is placed individually in a metabolic cage equipped with a funnel and a graduated glass cylinder to collect urine for four hours. Urine volume is measured and osmolality analyzed by use of a Fiske One-Ten osmometer (Fiske Assoc., Norwood, Mass., USA). Urinary sodium, potassium, and chloride are analyzed by use of ion-specific electrodes in a Beckman E3 (Electrolyte 3) Analyzer.

In the following results, decreased urine volume and decreased osmolality relative to AVP-control indicates activity. The results of this test on representative compounds of this invention are shown in Table II.

TABLE II

Vasopressin V2 Antagonist Activity In Conscious Hydrated Rats

| Ex. No. | Dose (mg/kg) | N | Urine Volume (ml/4 hrs) | Osmolality (mOsm/kg) |
| --- | --- | --- | --- | --- |
| * | | 78 | 13.3 ± 0.3 | 229 ± 6 |
| ** | | 6 | 12.1 ± 1 | 497 ± 53 |
| | | 4 | 12.4 ± 0.8 | 361 ± 30 |
| *** | | 76 | 2 ± 0.2 | 1226 ± 58 |
| 1 | 10 | 2 | 5 | 1148 |
| 2 | 10 | 2 | 5.5 | 1257 |
| 3 | 10 | 2 | 5.9 | 1205 |
| 4 | 10 | 3 | 6.3 | 1033 |
| 5 | 10 | 2 | 7.8 | 992 |
| 7 | 10 | 2 | 7.5 | 1005 |
| 8 | 10 | 2 | 8 | 887 |
| 9 | 10 | 2 | 8.3 | 857 |
| 11 | 10 | 2 | 11 | 825 |
| 12 | 10 | 2 | 5.8 | 1254 |
| 13 | 10 | 2 | 5.5 | 1380 |
| 14 | 10 | 2 | 4 | 1247 |
| 15 | 10 | 2 | 4 | 1278 |
| 16 | 10 | 2 | 6 | 1022 |
| 17 | 10 | 2 | 10.3 | 929 |
| 18 | 10 | 2 | 5.3 | 919 |
| 19 | 10 | 2 | 3.5 | 1598 |
| 20 | 10 | 2 | 3.5 | 1650 |
| 21 | 10 | 2 | 4.5 | 1347 |

*Water-load control
**Water-load Control + DMSO (10%)
***AVP-control

Vasopressin $V_1$ Antagonist Activity in Conscious Rats

Conscious rats are restrained in a supine position with elastic tape. The area at the base of the tail is locally anesthetized by subcutaneous in filtration with 2% procaine (0.2 ml). Using aseptic technique the ventral caudal tail artery is isolated and a cannula made of PE 10 and 20 (heat-fused) tubing is passed into the lower abdominal aorta. The cannula is secured, heparinized (1000 i.u./cc), sealed and the wound closed with one or two stitches of Dexon 4-0. The caudal vein is also cannulated in the same manner for intravenous drug administration. The duration of the surgery is approximately 5 minutes. Additional local anesthesia (2% procaine or lidocaine) is provided as needed.

The animals are placed in plastic restraining cages in an upright position. The cannula is attached to a Statham P23Db pressure transducer and pulsatile blood pressure is recorded. Increase of systolic blood pressure responses to arginine vasopressin 0.01 and 0.2 international unit (I.U.)(350 I.U.=1 mg) injections are recorded prior to any drug (compound) administration, after which each rat is dosed orally with compounds under study 0.1–100 mg/kg (10 cc/kg) or intravenously 0.1–30 mg/kg (1 cc/kg). The vasopressin injections are repeated 30,60,90,120,180,240 and 300 min. later. Percentage of antagonism by the compound is calculated using the pre-drug vasopressin vasopressor response as 100%.

The results of this test on representative compounds of this invention in which the dose, the maximum % inhibition and the time in minutes, are shown in Table III.

TABLE III

VASOPRESSIN (VAS) VASOPRESSOR RESPONSE

| Ex. No. | Dose mg/kg | Max % Inhibition | Time (min) |
| --- | --- | --- | --- |
| 1 | 30 po | 53 | 120 |
| 3 | 10 iv | 92 | 30 |
| 4 | 30 iv | 30 | 90 |
| 7 | 10 iv | 90 | 30 |
| 9 | 10 iv | 70 | 30 |
| 11 | 30 iv | 54 | 300 |
| 14 | 30 iv | 50 | 90 |
| 16 | 10 iv | 67 | 240 |
| 17 | 30 iv | 63 | 60 |
| 18 | 30 iv | 36 | 300 |
| 19 | 10 iv | 60 | 30 |
| 20 | 10 iv | 61 | 240 |

Oxytocin Receptor Binding (a) Membrane Preparation

Female Sprague-Dawley rats weighing approximately 200–250 g are injected intramuscularly (i.m.) with 0.3 mg/kg of body weight of diethylstilbestrol (DES). The rats are sacrificed 18 hours later under pentobarbital anesthesia. The uteri are dissected out, cleaned of fat and connective tissues and rinsed in 50 ml of normal saline. The tissue pooled from six rats is homogenized in 50 ml of 0.01 mM Tris.HCl, containing 0.5 mM dithiothreitol and 1.0 mM EDTA, adjusted to pH 7.4, using a polytron at setting 6 with three passes of 10 sec each. The homogenate is passed through two (2) layers of cheesecloth and the filtrate centrifuged at 1000× g for 10 min. The clear supernatant is removed and recentrifuged at 165,000× g for 30 min. The resulting pellet containing the oxytocin receptors is resuspended in 50.0 mM Tris.HCl containing 5.0 mM $MgCl_2$ at pH 7.4, to give a protein concentration of 2.5 mg/ml of tissue suspension. This preparation is used in subsequent binding assays with [$^3$H]Oxytocin.

(b) Radioligand Binding

Binding of 3,5-[$^3$H]Oxytocin ([$^3$H]OT) to its receptors is done in microtiter plates using [$^3$H]OT, at various concentrations, in an assay buffer of 50.0 mM Tris.HCl, pH 7.4 and containing 5.0 mM $MgCl_2$, and a mixture of protease inhibitors: BSA, 0.1 mg; aprotinin, 1.0 mg; 1,10-phenanthroline, 2.0 mg; trypsin, 10.0 mg; and PMSF, 0.3 mg per 100 ml of buffer solution. Non-specific binding is determined in the presence of 1.0 uM unlabeled OT. The binding reaction is terminated after 60 min., at 22° C., by rapid filtration through glass fiber filters using a Brandel, cell harvester (Biomedical Research and Development Laboratories, Inc., Gaithersburg, Md.). Competition experiments are conducted at equilibrium using 1.0 nM [$^3$H]OT and varying the concentration of the displacing agents. The concentrations of agent displacing 50% of [$^3$H]OT at its sites ($IC_{50}$) are calculated by a computer assisted LUNDON-2 program (LUNDON SOFTWARE INC., Ohio, USA).

The results of this assay on representative examples are shown in Table IV.

TABLE IV

Oxytocin Binding Assay

| Ex. No. | Dose (μM) | % Inhibition at 10 μM | IC$_{50}$ (μM) |
|---|---|---|---|
| 2 | 10 | 100 | 0.049 ± 0.003 |
| 3 | 10 | 89 | 2.6 |
| 4 | 10 | 62 | |
| 6 | 10 | 100 | 0.33 |
| 7 | 10 | 100 | 0.23 |
| 8 | 10 | 95 | 1.27 |
| 9 | 10 | 100 | 0.13 |
| 10 | 10 | 77 | 2.5 |
| 11 | 10 | 86 | 1.8 |
| 12 | 10 | 69 | |
| 13 | 10 | 67 | |
| 14 | 10 | 67 | |
| 15 | 10 | 98 | 2.1 |
| 16 | 10 | 100 | 0.11 |
| 17 | 10 | 92 | 1.09 |
| 18 | 10 | 99 | 0.12 |
| 19 | 10 | 81 | 0.043 |
| 20 | 10 | 100 | 0.11 |
| 21 | 10 | 68 | |
| 22 | 10 | 98 | 0.48 |

The compounds of the present invention can be used in the form of salts derived from pharmaceutically or physiologically acceptable acids or bases. These salts include but are not limited to the following: salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium or with organic bases. The compounds can also be used in the form of esters, carbamates and other conventional "pro-drug" forms, which, when administered in such form, convert to the active moiety in vivo. When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxy propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The new tricyclic non-peptide vasopressin antagonists of this invention are useful in treating conditions where decreased vasopressin levels are desired, such as in congestive heart failure, in disease conditions with excess renal water reabsorption and in conditions with increased vascular resistance and coronary vasoconstriction.

In particular, the vasopressin antagonists of this invention are therapeutically useful in the treatment and/or prevention of hypertension, cardiac insufficiency, coronary vasospasm, cardiac ischemia, renal vasospasm, liver cirrhosis, congestive heart failure, nephritic syndrome, brain edema, cerebral ischemia, cerebral hemorrhage-stroke, thrombosis-bleeding and abnormal states of water retention.

In particular, the oxytocin antagonists of this invention are useful in the prevention of preterm labor and premature birth which is a significant cause of infant health problems and infant mortality.

What is claimed is:

1. A compound selected from Formula I:

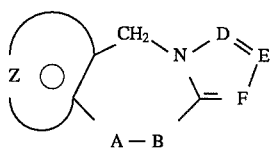

Formula I wherein;

the moiety:

is a fused phenyl ring optionally substituted by one or two substituents selected from ($C_1$-$C_3$) lower alkyl, halogen, amino, ($C_1$-$C_3$) lower alkoxy, or ($C_1$-$C_3$) lower alkyl amino;

A—B is

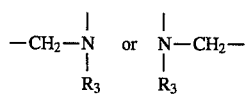

the moiety

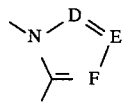

is a five membered aromatic (unsaturated) nitrogen containing heterocyclic ring wherein D, E, and F are selected from carbon and nitrogen and wherein the carbon atoms may be optionally substituted by a substituent selected from halogen, ($C_1$-$C_3$) lower alkyl, hydroxy, —$COCl_3$, —$COCF_3$,

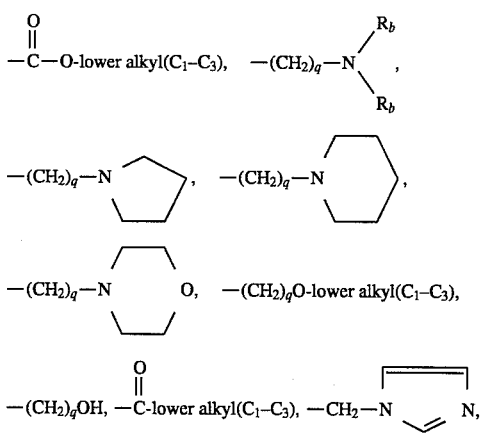

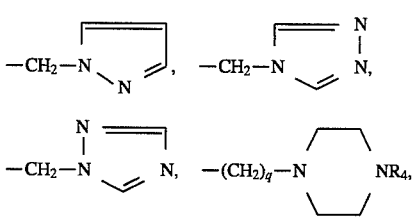

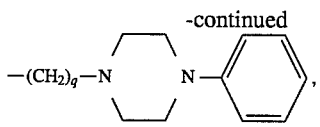

—CHO, amino, ($C_1$-$C_3$) lower alkoxy, ($C_1$-$C_3$) lower alkylamino, CONH-lower alkyl ($C_1$-$C_3$), —CON[lower alkyl ($C_1$-$C_3$)]$_2$;

q is one or two;

$R_b$ is independently selected from H, —$CH_3$, or —$C_2H_5$;

$R_3$ is a moiety of the formula

wherein Ar is a moiety selected from the group

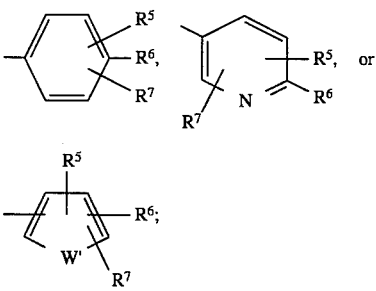

wherein $R^6$ is selected from

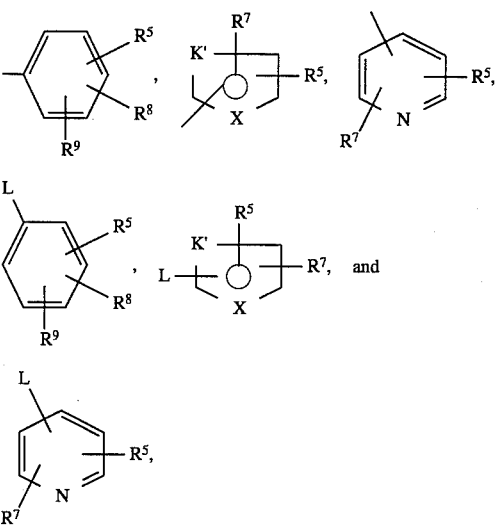

wherein

L is —O—, —S—, SO, —$SO_2$—, —CO—, —$CH_2$—, or —C≡C—;

K' is CH or N; X is O, S, or N-lower alkyl($C_1$-$C_3$);

W' is selected from O, S, NH, N-lower alkyl ($C_1$-$C_3$), and N-benzyl;

$R_4$ is selected from H, lower alkyl ($C_1$-$C_3$), and —CO-lower alkyl ($C_1$-$C_3$);

$R^5$ is selected from H, lower alkyl ($C_1$-$C_3$), lower alkoxy ($C_1$-$C_3$), —O—$CH_2$—$CH_2$=$CH_2$ and halogen;

$R^7$ is selected from H, lower alkyl ($C_1$-$C_3$), —O-lower alkyl ($C_1$-$C_3$), —$CF_3$ and halogen;

$R^8$ and $R^9$ are independently selected from H, lower alkyl ($C_1$–$C_3$), —S-lower alkyl ($C_1$–$C_3$), halogen, —NH-lower alkyl ($C_1$–$C_3$), $OCF_3$, —OH, —CN, —S—$CF_3$, —$NO_2$, —O-lower alkyl ($C_1$–$C_3$), —CO-lower alkyl ($C_1$–$C_3$), and $CF_3$; or a pharmaceutically acceptable salt, ester or pro-drug form thereof.

2. A compound according to claim 1 in which D, E, and F are carbon, or a pharmaceutically acceptable salt, ester or pro-drug form thereof.

3. A compound according to claim 1 in which D is nitrogen and E and F are carbon, wherein one of E or F is optionally substituted by a substituent selected from the group of halogen, lower alkyl ($C_1$–$C_3$), and lower alkoxy ($C_1$–$C_3$); or a pharmaceutically acceptable salt, ester or pro-drug form thereof.

4. A compound according to claim 1 which is 10,11-dihydro-10-[4-(2 -thienyl)benzoyl]-5H-pyrrolo[2,1-c][1,4]benzodiazepine or a pharmaceutically acceptable salt, ester or pro-drug form thereof.

5. A compound according to claim 1 which is 10,11-dihydro-10-[4-(2 -nitrophenyl)benzoyl]-5H-pyrrolo[2,1-c][1,4]benzodiazepine or a pharmaceutically acceptable salt, ester or pro-drug form thereof.

6. A compound according to claim 1 which is 10,11-dihydro-10-[4-(3,5 -difluorophenyl)benzoyl]-5H-pyrrolo[2,1-c][1,4]benzodiazepine or a pharmaceutically acceptable salt, ester or pro-drug form thereof.

7. A compound according to claim 1 which is 10,11-dihydro-10-[4 -(phenylethynyl)-5H-pyrrolo[2,1-c]1,4]benzodiazepine or a pharmaceutically acceptable salt, ester or pro-drug form thereof.

8. A compound according to claim 1 which is 10,11-dihydro-10-[4-(2 -methylphenyl)benzoyl]-5H-pyrrolo[2,1-c][1,4]benzodiazepine or a pharmaceutically acceptable salt, ester or pro-drug form thereof.

9. A compound according to claim 1 which is 10,11-dihydro-3 -[(dimethylamino)methyl]-10-[4-(2-thienyl)benzoyl]-5H-pyrrolo[2,1 -c][1,4]benzodiazepine or a pharmaceutically acceptable salt, ester or pro-drug form thereof.

10. A compound according to claim 1 which is 5-([1,1'-biphenyl]-4-ylcarbonyl)-5,10-dihydro-4H-pyrazolo[5,1-c][1,4]benzodiazepine or a pharmaceutically acceptable salt, ester or pro-drug form thereof.

11. A compound according to claim 1 which is 10,11-dihydro-10-[[2'-(trifluoromethyl)[1,1'-biphenyl]-4-yl]carbonyl-5H-pyrrolo[2,1-c][1,4]benzodiazepine or a pharmaceutically acceptable salt, ester or pro-drug form thereof.

12. A compound according to claim 1 which is 10,11-dihydro-10-[4-(2 -pyridinyl)benzoyl]-5H-pyrrolo[2,1-c][1,4]benzodiazepine or a pharmaceutically acceptable salt, ester or pro-drag form thereof.

13. A compound according to claim 1 which is 10,11-dihydro-10-[4-(2 -thiazolyl)benzoyl]-5H-pyrrolo[2,1-c][1,4]benzodiazepine or a pharmaceutically acceptable salt, ester or pro-drug form thereof.

14. A compound according to claim 1 which is 10,11-dihydro-10 -[4-(4-methylphenyl)thio]benzoyl-5H-pyrrolo[2,1-c][1,4]benzodiazepine or a pharmaceutically acceptable salt, ester or pro-drug form thereof.

15. A compound according to claim 1 which is 10,11-dihydro-10-[4 -phenylsulfonyl]benzoyl-5H-pyrrolo[2,1-c][1,4]benzodiazepine or a pharmaceutically acceptable salt, ester or pro-drug form thereof.

16. A compound according to claim 1 which is 10,11-dihydro-10-[4-[(4 -methylphenyl)sulfonyl]benzoyl]-5H-pyrrolo[2,1-c][1,4]benzodiazepine or a pharmaceutically acceptable salt, ester or pro-drug form thereof.

17. A compound according to claim 1 which is 10,11-dihydro-10-[4'-(2 -propenyloxy)[1,1'-biphenyl]-4-yl]carbonyl]-5H-pyrrolo[2,1-c][1,4]benzodiazepine or a pharmaceutically acceptable salt, ester or pro-drug form thereof.

18. A compound according to claim 1 which is 10,11-dihydro-10-[4 -(phenylthio)benzoyl]-5H-pyrrolo[2,1-c][1,4]benzodiazepine or a pharmaceutically acceptable salt, ester or pro-drug form thereof.

19. A compound according to claim 1 which is 10-(4-benzoylbenzoyl)- 10,11-dihydro-5H-pyrrolo[2,1-c][1,4]benzodiazepine or a pharmaceutically acceptable salt, ester or pro-drug form thereof.

20. A compound according to claim 1 which is 10,11-dihydro-10-[4-(4 -methylphenoxy)benzoyl]-5H-pyrrolo[2,1-c][1,4]benzodiazepine or a pharmaceutically acceptable salt, ester or pro-drug form thereof.

21. A compound according to claim 1 which is 10-([1,1'-biphenyl]-4 -ylcarbonyl)-10,11-dihydro-5H-pyrrolo[2,1-c][1,4]benzodiazepine or a pharmaceutically acceptable salt, ester or pro-drug form thereof.

22. A compound according to claim 1 which is 10-([1,1'-biphenyl]-4 -ylcarbonyl)-10,11-dihydro-N,N-dimethyl-5H-pyrrolo[2,1-c][1,4]benzodiazepine or a pharmaceutically acceptable salt, ester or pro-drug form thereof.

23. A compound according to claim 1 which is 10,11-dihydro-10-[(4'-propyl[1,1'-biphenyl]-4-yl)carbonyl]-5H-pyrrolo[2,1-c][1,4]benzodiazepine or a pharmaceutically acceptable salt, ester or pro-drug form thereof.

24. A compound according to claim 1 which is 10,11-dihydro-10-[5-[(2 -thienyl)pyridinyl]carbonyl]-5H-pyrrolo[2,1-c][1,4]benzodiazepine or a pharmaceutically acceptable salt, ester or pro-drug form thereof.

25. A pharmaceutical composition useful for treating disease in a mammal characterized by excess renal reabsorption of water, the pharmaceutical composition comprising an effective amount of a compound of claim 1, or a pharmaceutically acceptable salt, ester or prodrug form thereof, and a suitable pharmaceutical carrier.

26. The pharmaceutical composition of claim 25 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

27. A method for treating disease in a mammal characterized by excess renal reabsorption of water, the method comprising administering to a mammal in need thereof an effective amount of a compound of claim 1, or a pharmaceutically acceptable salt, ester or prodrug form thereof, and a suitable pharmaceutical carrier.

28. The method of claim 27 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

* * * * *

UNITED STATES PATENT AND TRADEMARK OFFICE
CERTIFICATE OF CORRECTION

PATENT NO. : 5,521,173
DATED     : May 28, 1996
INVENTOR(S) : Aranapkam M. Venkatesan, et al It is certified that error appears in the above-indentified patent and that said Letters Patent is hereby corrected as shown below:

Assignee:
On title page, insert item [73] to read as follows:
--American Cyanamid Company, Madison, N.J.--

Signed and Sealed this

Eleventh Day of February, 1997

Attest:

BRUCE LEHMAN

Attesting Officer

Commissioner of Patents and Trademarks